(12) United States Patent
Khan et al.

(10) Patent No.: US 7,517,529 B2
(45) Date of Patent: *Apr. 14, 2009

(54) TREATMENT OF TYPE I DIABETES

(75) Inventors: Nisar A. Khan, Rotterdam (NL); Robbert Benner, Barendrecht (NL)

(73) Assignee: Biotempt B.V., Koekange (NL)

( * ) Notice: Subject to any disclaimer, the term of this patent is extended or adjusted under 35 U.S.C. 154(b) by 245 days.

This patent is subject to a terminal disclaimer.

(21) Appl. No.: 11/243,438

(22) Filed: Oct. 4, 2005

(65) Prior Publication Data

US 2006/0111292 A1    May 25, 2006

Related U.S. Application Data

(63) Continuation of application No. PCT/EP2004/003747, filed on Apr. 8, 2004.

(30) Foreign Application Priority Data

| Apr. 8, 2003 | (EP) | 03076021 |
| Apr. 8, 2003 | (EP) | 03076022 |
| Apr. 8, 2003 | (EP) | 03076023 |
| Apr. 8, 2003 | (EP) | 03076024 |
| Apr. 8, 2003 | (EP) | 03076025 |
| Apr. 8, 2003 | (EP) | 03076026 |
| Apr. 8, 2003 | (EP) | 03076027 |
| Apr. 8, 2003 | (EP) | 03076028 |
| Apr. 8, 2003 | (EP) | 03076029 |
| Apr. 8, 2003 | (EP) | 03076030 |
| Apr. 30, 2003 | (CN) | 03 1 31227 |

(51) Int. Cl.
*A61K 39/00* (2006.01)
*A61K 38/00* (2006.01)

(52) U.S. Cl. .................................. 424/198.1; 530/300

(58) Field of Classification Search ........................ None
See application file for complete search history.

(56) References Cited

U.S. PATENT DOCUMENTS

| 4,977,244 | A | 12/1990 | Muchmore et al. |
| 5,380,668 | A | 1/1995 | Herron |
| 5,677,275 | A | 10/1997 | Lunardi-Iskandar et al. |
| 5,851,997 | A | 12/1998 | Harris |
| 5,877,148 | A | 3/1999 | Lunardi-Iskandar et al. |
| 5,958,413 | A | 9/1999 | Anagnostopulos et al. |
| 5,968,513 | A | 10/1999 | Gallo et al. |
| 5,997,871 | A | 12/1999 | Gallo et al. |
| 6,207,145 | B1 * | 3/2001 | Tovey ..................... 424/85.4 |
| 6,319,504 | B1 | 11/2001 | Gallo et al. |
| 6,489,296 | B1 | 12/2002 | Grinnell et al. |
| 6,583,109 | B1 | 6/2003 | Gallo et al. |
| 6,596,688 | B1 | 7/2003 | Gallo et al. |
| 6,620,416 | B1 | 9/2003 | Gallo et al. |
| 6,844,315 | B2 * | 1/2005 | Khan et al. .................. 514/2 |
| 6,921,751 | B1 * | 7/2005 | Khan et al. .................. 514/21 |
| 7,175,679 | B2 * | 2/2007 | Khan et al. .................. 514/2 |
| 2002/0041871 | A1 | 4/2002 | Brudnak |
| 2002/0064501 | A1 | 5/2002 | Khan et al. |
| 2003/0049273 | A1 | 3/2003 | Gallo et al. |
| 2003/0113733 | A1 | 6/2003 | Khan et al. |
| 2003/0119720 | A1 | 6/2003 | Khan et al. |
| 2003/0166556 | A1 | 9/2003 | Khan et al. |
| 2003/0186244 | A1 | 10/2003 | Margus et al. |
| 2003/0215434 | A1 | 11/2003 | Khan et al. |
| 2003/0219425 | A1 | 11/2003 | Khan et al. |
| 2003/0220257 | A1 | 11/2003 | Benner et al. |
| 2003/0220258 | A1 | 11/2003 | Benner et al. |
| 2003/0220259 | A1 | 11/2003 | Benner et al. |
| 2003/0220260 | A1 | 11/2003 | Khan et al. |
| 2003/0220261 | A1 | 11/2003 | Khan et al. |
| 2003/0224995 | A1 | 12/2003 | Khan et al. |
| 2004/0013661 | A1 | 1/2004 | Wensvoort et al. |

FOREIGN PATENT DOCUMENTS

| DE | 3715662 | 11/1987 |
| DE | 19953339 | 5/2001 |
| EP | 1 138 692 A1 | 10/2001 |
| EP | 1 300 418 | 4/2003 |
| FR | 2 706 772 | 12/1994 |
| WO | 96/04008 | 2/1996 |
| WO | 97/49373 | 12/1997 |
| WO | 97/49418 | 12/1997 |
| WO | 97/49432 | 12/1997 |
| WO | WO 97/49721 | 12/1997 |

(Continued)

OTHER PUBLICATIONS

Rodriguez M, et al. Expression of human HLA-B27 transgene alters susceptibility to murine theiler's virus-induced demylenination. 1991. vol. 146, p. 2596-2602.*
Huang Y, et al. Ischemia-reperfusion and immediate T cell responses. Cellular Immunology. 2007. vol. 248, p. 4-11.*
http://www.rxlist.com/cgi/generic/chorionic.htm—RxList.com entry for hCG/Pregnyl.*
NCBI Accession No. AAI06724, version Oct. 6, 2006.*

(Continued)

*Primary Examiner*—Robert Landsman
*Assistant Examiner*—Bruce D Hissong
(74) *Attorney, Agent, or Firm*—TraskBritt

(57) ABSTRACT

The invention relates to the field of immunology, more specifically to the field of immune-mediated disorders such as allergies, auto-immune disease, transplantation-related disease and other inflammatory diseases. The invention in particular relates to the systemic treatment of inflammatory disease by oral or mucosal administration of a pharmaceutical composition with a gene-regulatory peptide. The invention provides a pharmaceutical composition in a form for mucosal application for the treatment of a subject suffering from disease, the pharmaceutical composition comprising a pharmacologically effective amount of a gene-regulatory peptide or a functional analogue thereof together with a pharmaceutically acceptable diluent.

3 Claims, 1 Drawing Sheet

FOREIGN PATENT DOCUMENTS

| WO | WO 98/35691 | 8/1998 |
|----|-------------|--------|
| WO | WO 99/59617 | 11/1999 |
| WO | WO 01/10907 A2 | 2/2001 |
| WO | WO 01/11048 A2 | 2/2001 |
| WO | WO 01/68113 A1 | 9/2001 |
| WO | WO 01/72831 | 10/2001 |
| WO | WO 02/085117 | 10/2002 |
| WO | WO 03/029292 A2 | 4/2003 |
| WO | WO 2004/093897 A1 | 11/2004 |

OTHER PUBLICATIONS

Connelly et al., Biphasic Regulation of NF-κB Activity Underlies the Pro- and Anti-Inflammatory Actions of Nitric Oxide, The Journal of Immunology, 2001, pp. 387381, 166, The American Association of Immunologists, USA.

Friedlander, Tackling anthrax, Nature, Nov. 8, 2001, pp. 160-161, vol. 414.

Medzhitov, Toll-like Receptors and Innate Immunity, Nature Reviews/Immunology, Nov. 2001, pp. 135-145, vol. 1.

Lang et al., "Induction of apoptosis in Kaposi's sarcoma spindle cell cultures by the subunits of human chorionic gonadotropin", AIDS 1997, vol. 11, No. 11, pp. 1333-1340.

Iskandar et al., "Effects of a urinary factor from women in early pregnancy on HIVI. SIV and associated disease", Nature Medicine, Apr. 1998, vol. 4, No. 4, pp. 428-434.

Christman et al., Nuclear factor kappaB: a pivotal role in the systemic inflammatory response syndrome and new target for therapy, Intens Care Med, 1998, pp. 1131-1138, vol. 24.

Jyonouchi et al., Proinflammatory and regulatory cytokine production associated with innate and adaptive immune responses in children with autism spectrum disorders and developmental regression, J Neuroim., 2001, pp. 170-179, vol. 120.

Kanungo et al., Advanced Maturation of *Heteropneustes fossilis* (Bloch) by Oral Administration of Human Chorionic Gonadotropin, J. Adv. Zool., 1999, pp. 1-5, vol. 20.

Rohrig et al., Growth-stimulating Influence of Human Chorionic Gonadotropin (hCG) on *Plasmodium falciparum* in vitro, Zentralblatt Bakt, 1999, pp. 89-99, vol. 289.

Tak et al., NF-kappaB: a key role in inflammatory diseases, J Clin Invest., 2001, pp. 7-11, vol. 107.

Tan et al., The role of activation of nuclear factor-kappa B of rat brain in the pathogenesis of experimental allergic encephalomyelitis, Acta Physiol Sinica, 2003, pp. 58-64, vol. 55.

Tovey et al., Mucosal Cytokine Therapy: Marked Antiviral and Antitumor Activity, J. Interferon Cytokine Res., 1999, pp. 911-921, vol. 19.

Albini, A., et al., "Old drugs as novel angiogenesis inhibitors: Preclinical studies with NAC, hCG, EGCG and somatostatin," 17 Clinical & Experimental Metastasis 739 (1999).

Blackwell, Timothy S., et al., "The Role of Nuclear Factor-kB in Cytokine Gene Regulation," 17 Am. J. Respir. Cell Mol. Biol. 3-9 (1997).

Keller, S., et al., "Human Chorionic Gonadotropin (hCG) Is a Potent Angiogenic Factor for Utrine Endothelial Cells in Vitro," 20(5-6) Placenta, p. A37 (Jul. 1999).

Khan, Nisar A., et al., "Inhibition of Diabetes in NOD Mice by Human Pregnancy Factor," 62(12) Human Immunology 1315-1323 (Dec. 2001).

Khan, Nisar A., et al., "Inhibition of Septic Shock in Mice by an Oligopeptide From the β-Chain of Human Chorionic Gonadotrophin Hormone," 63(1) Human Immunology 1-7 (Jan. 2002).

Muchmore et al., Immunoregulatory Properties of Fractions from Human Pregnancy Urine: Evidence that Human Chorionic Gonadotropin is not Responsible, The Journal of Immunology, Mar. 1997, pp. 881-886, vol. 118, No. 3.

Muchmore et al., Purification and Characterization of a MannoseContaining Disaccharide Obtained from Human Pregnancy Urine, Journal of Experimental Medicine, Dec. 1984, pp. 1672-1685, vol. 160.

Patil, A., et al., "The Study of the Effect of Human Chorionic Gonadotrophic (HCG) Hormone on the Survival of Adrenal Medulla Transplant in Brain. Preliminary Study," 87 Acta Neurochir (Wien) 76-78 (1987).

Slater, Lewis M., et al., "Decreased Mortality of Murine Graft-Versus-Host Disease by Human Chorionic gonadotropin,"23(1) Transplantation 103-104 (Jan. 1977).

Wulczyn, F. Gregory, et al., "The NF-κB/Rel and IκB gene families mediators of immune response and inflammation," 74(12) J. Mol. Med. 749-769 (1996).

Yamamoto, Y., et al., "Role of the NF-κB Pathway in the Pathogenesis of Human Disease States," 1(3) Current Molecular Medicine 287-296 (Jul. 2001).

Kachra et al., "Low Molecular Weight Components but Not Dimeric HCG Inhibit Growth and Down-Regulate AP-1 Transcription Factor in Kaposi's Sarcoma Cells," Endocrinology, 1997, pp. 4038-4041, vol. 138, No. 9.

Ivanov et al., "Hemoglobin as a Source of Endogenous Bioactive Peptides: The Concept of Tissue-Specific Peptide Pool," Biopolymers, 1997, pp. 171-188, vol. 39.

Khavinson et al, Gerontological Aspects of Genome Peptide Regulation, 2005, S. Karger AG, Basel, Switzerland.

Khavinson et al., "Effects of Livagen Peptide on Chromatin Activation in Lymphocytes from Old People," Bulletin of Experimental Biology and Medicine, Oct. 2002, pp. 389-392, vol. 134, No. 4.

Khavinson et al., "Effects of Short Peptides on Lymphocyte Chromatin in Senile Subjects," Bulletin of Experimental Biology and Medicine, Jan. 2004, pp. 78-81, vol. 137, No. 1.

Khavinson et al., "Epithalon Peptide Induces Telomerase Activity and Telomere Elongation in Human Somatic Cells," Bulletin of Experimental Biology and Medicine, Jun. 2003, pp. 590-592, vol. 135, No. 6.

Khavinson et al., "Inductive Activity of Retinal Peptides," Bulletin of Experimental Biology and Medicine, Nov. 2002, pp. 482-484, vol. 134, No. 5.

Khavinson et al., "Mechanisms Underlying Geroprotective Effects of Peptides," Bulletin of Experimental Biology and Medicine, Jan. 2002, pp. 1-5, vol. 133, No. 1.

Khavinson et al., "Peptide Promotes Overcoming of the Division Limit in Human Somatic Cell," Bulletin of Experimental Biology and Medicine, May 2004, pp. 503-506, vol. 137, No. 5.

Morozov et al., "Natural and Synthetic Thymic Peptides as Therapeutics for Immune Dysfunction," Int. J. Immunopharmac., 1997, pp. 501-505, vol. 19, No. 9/10.

* cited by examiner

Mucosal treatment with gene regulatory peptides 4+5+6 (experiment 3) significantly increased the percentage of MP12/20 high positive bone marrow cells

TREATMENT OF TYPE I DIABETES

CROSS-REFERENCE TO RELATED APPLICATIONS

This application is a continuation of PCT International Patent Application No. PCT/EP2004/003747, filed on Apr. 8, 2004, designating the United States of America, and published, in English, as PCT International Publication No. WO 2004/093897 on Nov. 4, 2004, the contents of the entirety of which are incorporated by this reference, which international application itself claims priority to EP 03076028.4, filed Apr. 8, 2003 with the European Patent Office (EPO), EP 03076029.2, filed Apr. 8, 2003 with the EPO, of EP 03076027.6, filed Apr. 8, 2003, with the EPO, of EP 03076026.8, filed Apr. 8, 2003 with the EPO, of EP 03076022.7 filed Apr. 8, 2003 with the EPO, of EP 03076021.9, filed Apr. 8, 2003 with the EPO, of EP 03076025.0, filed Apr. 8, 2003 with the EPO, of EP 03076024.3, filed Apr. 8, 2003 with the EPO, of EP 03076030.0, filed Apr. 8, 2003 with the EPO, of EP 03076023.5, filed Apr. 8, 2003 with the EPO, and of CN 03131227.6, filed Apr. 30, 2003 with the Chinese Patent Office.

TECHNICAL FIELD

The invention relates generally to biotechnology and to the field of immunology, more specifically to the field of immune-mediated disorders such as allergies, auto-immune disease, transplantation-related disease and other inflammatory diseases. The invention in particular relates to the treatment of inflammatory disease by administration of a pharmaceutical composition with a gene-regulatory peptide.

BACKGROUND

The immune system produces cytokines and other humoral and cellular factors to respond with an inflammation to protect the host when threatened by noxious agents, microbial invasion, or injury. In most cases this complex defense network successfully restores normal homeostasis, but at other times the immunological or inflammatory mediators may actually prove deleterious to the host. Some examples of immune disease and immune system-mediated injury have been extensively investigated including anaphylactic shock, autoimmune disease, and immune complex disorders.

Recent advances in humoral and cellular immunology, molecular biology and pathology have influenced current thinking about auto-immunity being a component of immune-mediated inflammatory disease. These advances have increased our understanding of the basic aspects of antibody, B-cell, and T-cell diversity, the generation of innate (effected by monocytes, macrophages, granulocytes, natural killer cells, mast cells, γδ T-cells, complement, acute phase proteins, and such) and adaptive (T- and B-cells and antibodies) or cellular and humoral immune responses and their interdependence, the mechanisms of (self)-tolerance induction and the means by which immunological reactivity develops against auto-antigenic constituents.

Since 1900, the central dogma of immunology has been that the immune system does not normally react to self. However, it has recently become apparent that auto-immune responses are not as rare as once thought and that not all auto-immune responses are harmful; some responses play a distinct role in mediating the immune response in general. For example, certain forms of auto-immune response such as recognition of cell surface antigens encoded by the major histocompatibility complex (MHC) and of anti-idiotypic responses against self idiotypes are important, indeed essential, for the diversification and normal functioning of the intact immune system.

Apparently, an intricate system of checks and balances is maintained between various subsets of cells (i.e., T-cells) of the immune system, thereby providing the individual with an immune system capable of coping with foreign invaders. In that sense, auto-immunity plays a regulating role in the immune system.

However, it is now also recognized that an abnormal auto-immune response is sometimes a primary cause and at other times a secondary contributor to many human and animal diseases. Types of auto-immune disease frequently overlap, and more than one auto-immune disorder tends to occur in the same individual, especially in those with auto-immune endocrinopathies. Auto-immune syndromes may be mediated with lymphoid hyperplasia, malignant lymphocytic or plasma cell proliferation and immunodeficiency disorders such as hypogammaglobulinaemia, selective Ig deficiencies and complement component deficiencies.

Auto-immune diseases, such as systemic lupus erythematosus, diabetes, rheumatoid arthritis, post-partum thyroid dysfunction, auto-immune thrombocytopenia, to name a few, are characterized by auto-immune inflammatory responses, for example, directed against widely distributed self-antigenic determinants, or directed against organ- or tissue-specific antigens. Such disease may follow abnormal immune responses against only one antigenic target, or against many self antigens. In many instances, it is not clear whether auto-immune responses are directed against unmodified self-antigens or self-antigens that have been modified (or resemble) any of numerous agents such as viruses, bacterial antigens and haptenic groups.

There is as yet no established unifying concept to explain the origin and pathogenesis of the various auto-immune disorders. Studies in experimental animals support the notion that auto-immune diseases may result from a wide spectrum of genetic and immunological abnormalities which differ from one individual to another and may express themselves early or late in life depending on the presence or absence of many superimposed exogenous (viruses, bacteria) or endogenous (hormones, cytokines, abnormal genes) accelerating factors. However, one common aspect of all these various disease comes to the eye; all share a, at times mostly systemic, inflammatory response.

It is evident that similar checks and balances that keep primary auto-immune disease at bay are also compromised in other immune-mediated disorders, such as allergy (asthma), acute inflammatory disease such as sepsis or septic shock, chronic inflammatory disease (i.e., rheumatic disease, Sjögrens syndrome, multiple sclerosis), transplantation-related inflammatory responses (graft-versus-host-disease, post-transfusion thrombocytopenia), and many others wherein the responsible antigens (at least initially) may not be self-antigens but wherein the inflammatory response is in principle not wanted and detrimental to the individual.

As a particular example of an acute systemic inflammatory response, the sepsis/SIRS concept is here discussed. Sepsis is a syndrome in which immune mediators, induced by, for example, microbial invasion, injury or through other factors, induce an acute state of inflammation which leads to abnormal homeostasis, organ damage and eventually to lethal shock. Sepsis refers to a systemic response to serious infection. Patients with sepsis usually manifest fever, tachycardia, tachypnea, leukocytosis, and a localized site of infection.

Microbiologic cultures from blood or the infection site are frequently, though not invariably, positive. When this syndrome results in hypotension or multiple organ system failure (MOSF), the condition is called sepsis or septic shock. Initially, micro-organisms proliferate at a nidus of infection. The organisms may invade the bloodstream, resulting in positive blood cultures, or might grow locally and release a variety of substances into the bloodstream. Such substances, when of pathogenic nature are grouped into two basic categories: endotoxins and exotoxins. Endotoxins typically consist of structural components of the micro-organisms, such as teichoic acid antigens from staphylococci or endotoxins from gram-negative organisms like LPS). Exotoxins (e.g., toxic shock syndrome toxin-1, or staphylococcal enterotoxin A, B or C) are synthesized and directly released by the micro-organisms. As suggested by their name, both of these types of bacterial toxins have pathogenic effects, stimulating the release of a large number of endogenous host-derived immunological mediators from plasma protein precursors or cells (monocytes/macrophages, endothelial cells, neutrophils, T-cells, and others). Sepsis/SIRS is an acute systemic inflammatory response to a variety of noxious insults (particularly insults of an infectious origin such as a bacterial infection, but also non-infectious insults are well known and often seen). The systemic inflammatory response seen with sepsis/SIRS is caused by immunological processes that are activated by a variety of immunological mediators such as cytokines, chemokines, nitric oxide, and other immune mediating chemicals of the body. These immunological mediators are generally seen to cause the life-threatening systemic disease seen with sepsis/SIRS. These immunological mediators are, on the one hand, required locally, for example, as effective antibacterial response, but are, in contrast, potentially toxic when secreted into the circulation. When secreted into the circulation, these mediators can cause, in an upward spiral of cause and effect, the further systemic release of these mediators, in the end leading to severe disease, such as multiple organ failure and death. Crucial inflammatory mediators are tumor necrosis factor-$\alpha$ (TNF-$\alpha$), tissue growth factor-$\beta$ (TGF-$\beta$), interferon $\gamma$, interleukins (IL-1, IL-4, IL-5, IL-6, IL-10, IL-12, IL-23, IL-40, and many others), nitric oxide (NO), arachidonic acid metabolites and prostaglandins 1 and 2 (PGE1 and PGE2), and others.

In essence, sepsis, or septicemia, relates to the presence in the blood of pathogenic microorganisms or their toxins in combination with a systemic inflammatory disease associated with such presence. Central in the development of sepsis in a subject is an infection of a subject with a microorganism which gives origin to the systemic release of immunological mediators by its presence in the blood of an affected subject or by the presence of its toxins in the blood of the subject. Only when the presence gives rise to a disease that pertains to or affects the body as a whole, a systemic disease, one speaks of sepsis.

The field of sepsis is thus limited to those conditions that are characterized by the presence of microorganisms or their toxins in the blood of a subject and simultaneously to (respectively) the subject's systemic response(s) to the microorganism or to a subject's systemic response(s) toxins. Sepsis herein includes severe sepsis and septic shock, whereby severe sepsis relates to sepsis accompanied with organ dysfunction and septic shock relates to sepsis accompanied with hypotension or perfusion abnormalities or both. SIRS relates to the type of severe systemic disease seen in cases of sepsis but also relates to systemic inflammatory disease wherein pathogenic microorganisms or their toxins are not present in the blood.

Central in the development of SIRS in a subject is the presence and effects of immunological mediators that give rise to a disease that pertains to or affects the body as a whole, a systemic disease. This systemic immunological response can be caused by a variety of clinical insults, such as trauma, burns and pancreatitis. Also, burn patients with or without inhalation injury commonly exhibit a clinical picture produced by systemic inflammation. The phrase "systemic" inflammatory response syndrome (SIRS) has been introduced to designate the signs and symptoms of patients suffering from such a condition. SIRS has a continuum of severity ranging from the presence of tachycardia, tachypnea, fever and leukocytosis, to refractory hypotension and, in its most severe form, shock and multiple organ system dysfunction. In thermally injured patients, the most common causes of SIRS are the burn itself. Sepsis, SIRS with the presence of infection or bacteremia, is also a common occurrence. Pathological alterations of metabolic, cardiovascular, gastrointestinal, and coagulation systems occur as a result of the hyperactive immune system. Both cellular and humoral mechanisms are involved in these disease processes and have been extensively studied in various burn and sepsis models. The phrase systemic inflammatory response syndrome (SIRS) was recommended by the American College of Chest Physicians/Society for Critical Care Medicine (ACCP/SCCM) consensus conference in 1992 to describe a systemic inflammatory process, independent of its cause. The proposal was based on clinical and experimental results indicating that a variety of conditions, both infectious and noninfectious (i.e., burns, ischemia-reperfusion injury, multiple trauma, pancreatitis), induce a similar host response. Two or more of the following conditions must be fulfilled for the diagnosis of SIRS to be made:

Body temperature >38° C. or <36° C.;
Heart rate >90 beats/minute;
Respiratory rate >20/minute or $Paco_2$<32 mmHg;
Leukocyte count >12.000/$\mu$l, <4000/$\mu$L, or >10% immature (band) forms.

All of these pathophysiologic changes must occur as an acute alteration from baseline in the absence of other known causes for them such as chemotherapy-induced neutropenia and leukopenia.

As a particular representative of a subacute or chronic systemic inflammatory response, the clinical symptoms seen with an auto-immune inflammatory disease such as diabetes are here discussed. The non-obese diabetic (NOD) mouse is a model for auto-immune disease, in this case insulin-dependent diabetes mellitus (IDDM) which main clinical feature is elevated blood glucose levels (hyperglycemia). The elevated blood glucose level is caused by auto-immune inflammatory destruction of insulin-producing $\beta$-cells in the islets of Langerhans of the pancreas. This is accompanied by a massive cellular infiltration surrounding and penetrating the islets (insulitis) composed of a heterogeneous mixture of CD4+ and CD8+ T-lymphocytes, B-lymphocytes, macrophages and dendritic cells. Also in subacute and chronic inflammation, crucial inflammatory mediators are tumor necrosis factor-$\alpha$ (TNF-$\alpha$), tissue growth factor-$\beta$ (TGF-$\beta$), interferon $\gamma$, interleukins (IL-1, IL-4, IL-5, IL-6, IL-10, IL-12, IL-23, IL-40), nitric oxide (NO), arachidonic acid metabolites and prostaglandins 1 and 2 (PGE1 and PGE2), and others.

The NOD mouse represents a model in which a primary inflammatory response mediated by inflammatory mediators and directed against $\beta$-cells is the primary event in the development of IDDM. When the NOD mouse is not yet diabetic, an inflammation invariably directed at the $\beta$-cells develops. Diabetogenesis is mediated through a multifactorial interaction between a unique MHC class II gene and multiple, unlinked, genetic loci, as in the human disease. Moreover, the NOD mouse demonstrates beautifully the critical interaction between heredity and environment, and between primary and secondary inflammatory responses, its clinical manifestation, for example, depending on various external conditions, most importantly of the microorganism load of the environment in which the NOD mouse is housed. During the diabetic phase, the inflammatory responses in the mice (and humans suffering from established diabetes) are much more diverse, due to the vascular damage caused by the high glucose levels tissue damage results throughout the body, again inflammatory mediators get released and secondary inflammations flourish, resulting in inflammation throughout whole body, however, with much more serious consequences to the patient than the earlier phase at first sight seems to cause.

As for auto-immunity demonstrable in NOD mice, most antigen-specific antibodies and T-cell responses which are measured directed against various antigens were detected as self-antigens in diabetic patients. Understanding the role these auto-antigens play in NOD diabetes allows to further distinguish between an initial inflammatory response directed at pathogenic auto-antigens leading to the diabetic phase per se and the secondary inflammatory responses that are observed as an epiphenomenon.

In general, T-lymphocytes play a pivotal role in initiating the immune-mediated disease process. CD4+ T-cells can be separated into at least two major subsets Th1 and Th2. Activated Th1 cells secrete IFN-γ and TNF-α, while Th2 cells produce IL-4, IL-5 and IL-10. Th1 cells are critically involved in the generation of effective cellular immunity, whereas Th2 cells are instrumental in the generation of humoral and mucosal immunity and allergy, including the activation of eosinophils and mast cells and the production of IgE. A number of studies have now correlated diabetes in mice and human with Th1 phenotype development. On the other hand, Th2 T-cells are shown to be relatively innocuous. Some have even speculated that Th2 T-cells in fact, may be protective. It was shown that the ability of CD4+ T-cells to transfer diabetes to naive recipients resided not with the antigen specificity recognized by the TCR per se, but with the phenotypic nature of the T-cell response. Strongly polarized Th1 T-cells transferred disease into NOD neonatal mice, while Th2 T-cells did not, despite being activated and bearing the same TCR as the diabetogenic Th1 T-cell population. Moreover, upon co-transfer, Th2 T-cells could not ameliorate the Th1-induced diabetes, even when Th2 cells were co-transferred in ten-fold excess.

In summary, the crucial pathophysiologic event that precipitates acute as well as systemic inflammation is tissue damage after which inflammatory mediators, in particular cytokines, are released that initiate the inflammatory process. This can occur as a result of the direct injury to tissues from mechanical or thermal trauma as well as cellular injury induced by immunological or inflammatory mediators such as seen after, for example, ischemia-reperfusion injury or during a microbial infection of the tissue. Cellular injury results in the acute release of proinflammatory cytokines. If injury is severe, such as in extensive tissue damage, a profound release of cytokines occurs, resulting in the induction of a systemic inflammatory reaction. The ability of the host to adapt (acutely or chronically) to this systemic inflammatory response is dependent on the magnitude of the response, the duration of the response, and the adaptive capacity of the host.

The current invention relates to the body's innate way of modulation of important physiological processes and builds on insights reported in WO99/59617, WO01/72831 and PCT/NL02/00639.

In these earlier applications small gene-regulatory peptides are described that are present naturally in pregnant women and are derived from proteolytic breakdown of placental gonadotropins such as human chorionic gonadotropin (hCG) produced during pregnancy. These peptides (in their active state often only at about 4 to 6 amino acids long) were shown to have unsurpassed immunological activity that they exert by regulating expression of genes encoding inflammatory mediators such as cytokines. Surprisingly, it was found that breakdown of hCG provides a cascade of peptides that help maintain a pregnant woman's immunological homeostasis. These peptides are nature's own substances that balance the immune system to assure that the mother stays immunologically sound while her fetus does not get prematurely rejected during pregnancy but instead is safely carried through its time of birth.

Where it was generally thought that the smallest breakdown products of proteins have no specific biological function on their own (except to serve as antigen for the immune system), it now emerges that the body in fact routinely utilizes the normal process of proteolytic breakdown of the proteins it produces to generate important gene-regulatory compounds, short peptides that control the expression of the body's own genes. Apparently the body uses a gene-control system ruled by small broken down products of the exact proteins that are encoded by its own genes.

It is long known that during pregnancy the maternal system introduces a status of temporary immuno-modulation which results in suppression of maternal rejection responses directed against the fetus. Paradoxically, during pregnancy, often the mother's resistance to infection is increased and she is found to be better protected against the clinical symptoms of various auto-immune diseases such as rheumatism and multiple sclerosis. The protection of the fetus can thus not be interpreted only as a result of immune suppression. Each of the above three applications have provided insights by which the immunological balance between protection of the mother and protection of the fetus can be understood.

It was shown that certain short breakdown products of hCG (i.e., short peptides which can easily be synthesized, if needed modified, and used as pharmaceutical composition) exert a major regulatory activity on pro- or anti-inflammatory cytokine cascades that are governed by a family of crucial transcription factors, the NFκB family which stands central in regulating the expression of genes that shape the body's immune response.

Most of the hCG produced during pregnancy is produced by cells of the placenta, the exact organ where cells and tissues of mother and child most intensely meet and where immuno-modulation is most needed to fight off rejection. Being produced locally, the gene-regulatory peptides which are broken down from hCG in the placenta immediately balance the pro- or anti-inflammatory cytokine cascades found in the no-mans land between mother and child. Being produced by the typical placental cell, the trophoblast, the peptides traverse extracellular space; enter cells of the immune system and exert their immuno-modulatory activity by modulating NFκB-mediated expression of cytokine genes, thereby keeping the immunological responses in the placenta at bay.

SUMMARY OF THE INVENTION

It is herein postulated that the beneficial effects seen on the occurrence and severity of auto-immune disease in the pregnant woman result from an overspill of the hCG-derived peptides into the body as a whole; however, these effects must not be overestimated, as it is easily understood that the further away from the placenta, the less immuno-modulatory activity aimed at preventing rejection of the fetus will be seen, if only because of a dilution of the placenta-produced peptides throughout the body as a whole. However, the immuno-modulatory and gene-regulatory activity of the peptides should by no means only be thought to occur during pregnancy and in the placenta; men and women alike produce hCG, for example, in their pituitaries, and nature certainly utilizes the gene-regulatory activities of peptides in a larger whole.

Consequently, a novel therapeutic inroad is provided, using the pharmaceutical potential of gene-regulatory peptides and derivatives thereof. Indeed, evidence of specific up- or down-regulation of NFκB driven pro- or anti-inflammatory cytokine cascades that are each, and in concert, directing the body's immune response was found in silico in gene-arrays by expression profiling studies, in vitro after treatment of immune cells and in vivo in experimental animals treated with gene-regulatory peptides. Also, considering that NFκB is a primary effector of disease (A. S. Baldwin, *J. Clin. Invest.*, 2001, 107:3-6), using the hCG-derived gene-regulatory peptides offer significant potential for the treatment of a variety of human and animal diseases, thereby tapping the pharmaceutical potential of the exact substances that help balance the mother's immune system such that her pregnancy is safely maintained.

DETAILED DESCRIPTION OF THE INVENTION

Figure 1:
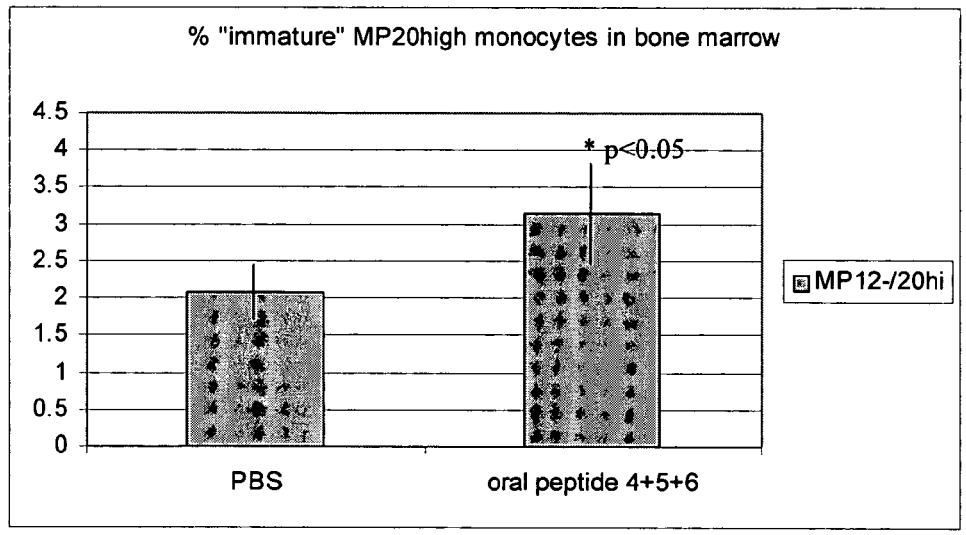
FIG. 1. Mucosal treatment with gene-regulatory peptides 4+5+6 (experiment 3, LQGV+GVLPALPQ+VLPALP (SEQ ID NOS:1, 23 and 4, respectively)) significantly increased the percentage of immature MP20 high positive bone marrow cells.
Figure 1:
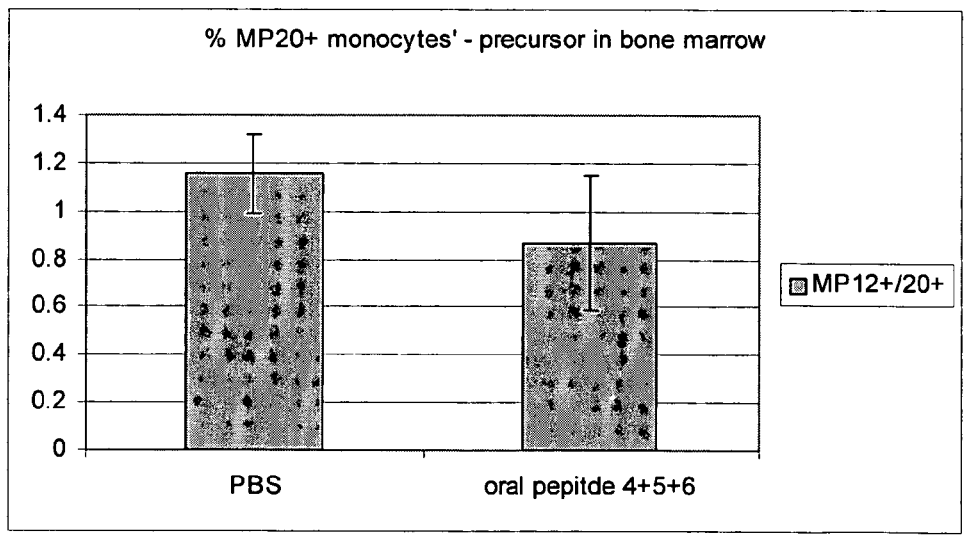

The invention provides the treatment of a subject suffering or believed to be suffering from disease by mucosal, preferably oral administration of a pharmaceutical composition comprising a pharmacologically effective amount of a gene-regulatory peptide or functional analogue thereof together with a pharmaceutically acceptable diluent to the subject. A particularly useful pharmaceutically acceptable diluent is sterile water or an isotonic salt solution such as 0.9% saline or phosphate buffered salt (PBS). In a preferred embodiment, the invention provides the treatment of a subject suffering or believed to be suffering from disease by mucosal, preferably oral administration of a pharmaceutical composition comprising a pharmacologically effective amount of two or more a gene-regulatory peptides or functional analogues thereof together with a pharmaceutically acceptable diluent to the subject. The administration dose of the gene-regulatory peptide may be varied over a fairly broad range. The concentrations of an active molecule which can be administered would be limited by efficacy at the lower end and the solubility of the compound at the upper end. The optimal dose or doses for a particular patient should and can be determined by taking into consideration relevant factors such as the condition, weight and age of the patient, and other considerations of the physician or medical specialist involved.

The invention thus provides use of a regulatory peptide pharmaceutical composition for mucosal, preferably oral application to a subject for generating a systemic modulation of the expression of a gene in a cell throughout the body of the subject. Useful examples of such a gene-regulatory peptide can be selected from the group of oligopeptides LQG, AQG, LQGV (SEQ ID NO:1), AQGV (SEQ ID NO:2), LQGA (SEQ ID NO:3), VLPALPQVVC (SEQ ID NO:21), VLPALP (SEQ ID NO:4), ALPALP (SEQ ID NO:5), VAPALP (SEQ ID NO:6), ALPALPQ (SEQ ID NO:7), VLPAAPQ (SEQ ID NO:8), VLPALAQ (SEQ ID NO:9), LAGV (SEQ ID NO:10), VLAALP (SEQ ID NO:11), VLPALA (SEQ ID NO:12), VLPALPQ (SEQ ID NO:13), VLAALPQ (SEQ ID NO:14), VLPALPA (SEQ ID NO:15), GVLPALP (SEQ ID NO:16), GVLPALPQ (SEQ ID NO:23), LQGVLPALPQVVC (SEQ ID NO:17), VVCNYRDVRFESIRLPGCPRGVNPV-VSYAVALSCQCAL (SEQ ID NO:24), RPRCRPINAT-LAVEK (amino acids 1-15 of SEQ ID NO:25), EGCPVCITVNTTICAGYCPT (amino acids 16-35 of SEQ ID NO:25), SKAPPPSLPSPSRLPGPS (SEQ ID NO:26), SIRLPGCPRGVNPVVS (SEQ ID NO:27), LPGCPRGVN-PVVS (SEQ ID NO:18), LPGC (SEQ ID NO:19), MTRV (SEQ ID NO:20), MTR, VVC, QVVC (SEQ ID NO:29) and functional analogues or derivatives thereof. Functional analogues can, for example, be found in urinary fractions derived from pregnant women or in commercial preparations of hCG; at least in those commercial preparations that contain substantial amounts of breakdown products of hCG and have gene-regulatory activity, however, a disadvantage of using such urinary fractions or even commercial hCG preparations lies in the fact that they may or not may contain (sufficient) quantities of the active compound, synthetic peptides are thus preferred.

A preferred size of a gene-regulatory peptide for inclusion in a pharmaceutical composition according to the invention is at most 15 amino acids, although much smaller molecules have been shown to be particularly effective. Surprisingly, the invention provides here the insight that gene expression can be modulated or regulated systemically by small peptides by applying them locally to the mucosae. Oral treatment is preferred, but mucosal treatment other than oral treatment is herein also provided. Preferred peptides are breakdown products of larger polypeptides such as chorionic gonadotrophin (CG) and growth hormones or growth factors such as fibroblast growth factor, EGF, VEGF, RNA 3' terminal phosphate cyclase and CAP18, or synthetic versions thereof. Preferred for oral treatment are peptides smaller then five amino acids, i.e., three or four amino acids long. In principle, such regulating peptide sequences can be derived from any protein of polypeptide molecule produced by prokaryotic and/or eukaryotic cells, and the invention provides the insight that breakdown products of polypeptides, preferably oligopeptides at about the sizes as provided herein that are naturally involved as gene-regulatory peptide in modulation of gene expression can be applied via the mucosa to generate a systemic effect. In particular, a (synthetic) gene-regulatory peptide is provided obtainable or derivable from β-human chorionic gonadotrophin (β-hCG), preferably from nicked β-HCG. It was thought before that breakdown products of β hCG were involved in immuno-modulation via regulation of gene expression (WO99/59671, WO01/72831, PCT/NL02/00639) or in the treatment of wasting syndrome (WO97/49721) but a relationship with systemic modulation of gene expression, in particular via local application at or through the mucosa was not forwarded in these publications. Of course, such a gene-regulatory peptide, or functional equivalent or derivative thereof, is likely obtainable or derivable from other proteins that are subject to breakdown or proteolysis and that are close to a gene-regulatory cascade. Preferably, the peptide signaling molecule is obtained from a peptide having at least 10 amino acids such as a peptide having an amino acid sequence MTRVLQGVLPALPQVVC (SEQ ID NO:30), SIRLPGCPRGVNPVVS (SEQ ID NO:27), VVCNYRDVR-FESIRLPGCPRGVNPVVSYAVALSCQCAL (SEQ ID NO:24), RPRCRPINATLAVEKEGCPVCITVNTTI-CAGYCPT (SEQ ID NO:25), CALCRRSTTDCGGPKDH-PLTC (SEQ ID NO:31), SKAPPPSLPSPSRLPGPS (SEQ ID NO:26), CRRSTTDCGGPKDHPLTC (SEQ ID NO:32), TCDDPRFQDSSSSKAPPPSLPSPSRLPGPSDTPILPQ (SEQ ID NO:33).

EXAMPLES

Not wishing to be bound by theory, it is postulated herein that an unexpected mode of gene regulation with far reaching consequences for the oral or mucosal treatment of disease has been uncovered. Polypeptides, such as endogenous CG, EGF, etc., but also polypeptides of pathogens such as viral, bacterial or protozoal polypeptides, are subject to breakdown into distinct oligopeptides, for example, by intracellular proteolysis. Distinct proteolytic enzymes are widely available in the cell, for example, in eukaryotes in the lysosomal or proteasomal system. Some of the resulting breakdown products are oligopeptides of 3 to 15, preferably 4 to 9, most preferably 4 to 6, amino acids long that are surprisingly not without any function or effect to the cell, but as demonstrated herein may be involved, possibly via a feedback mechanism in the case of breakdown of endogenous polypeptides, as signaling molecules in the regulation of gene expression, as demonstrated herein by the regulation of the activity or translocation of a gene transcription factor such as NFκB by, for example, peptides LQGV (SEQ ID NO:1), VLPALPQVVC (SEQ ID NO:21), LQGVLPALPQ (SEQ ID NO:17), LQG, GVL-PALPQ (SEQ ID NO:23), VLPALP (SEQ ID NO:4), VLPALPQ (SEQ ID NO:13), GVLPALP (SEQ ID NO:16), VVC, MTRV (SEQ ID NO:20), and MTR. Synthetic versions of these peptides as described above, and functional analogues or derivatives of these breakdown products, are herein provided to modulate gene expression in a cell and be used in methods to rectify errors in gene expression or the mucosal or oral treatment of systemic disease. Oligopeptides such as LQG, AQG, LQGV (SEQ ID NO:1), AQGV, LQGA (SEQ ID NO:3), VLPALP (SEQ ID NO:4), ALPALP (SEQ ID NO:5), VAPALP (SEQ ID NO:6), ALPALPQ (SEQ ID NO:7), VLPAAPQ (SEQ ID NO:8), VLPALAQ (SEQ ID NO:9), LAGV (SEQ ID NO:10), VLAALP (SEQ ID NO:11), VLPALA (SEQ ID NO:12), VLPALPQ (SEQ ID NO:13), VLAALPQ (SEQ ID NO:14), VLPALPA (SEQ ID NO:15), GVLPALP (SEQ ID NO:16), GVLPALPQ (SEQ ID NO:23), LQGVLPALPQVVC (SEQ ID NO: 17), SIRLPGCPRGVN-PVVS (SEQ ID NO:27), SKAPPPSLPSPSRLPGPS (SEQ ID NO:26), LPGCPRGVNPVVS (SEQ ID NO:18), LPGC (SEQ ID NO:19), MTRV (SEQ ID NO:20), MTR, VVC, or functional analogues or trimer or tetramer derivatives (including breakdown products) of the longer sequences thereof, are particularly effective. In particular, preferred for oral administration are LQG, QVV, PALP (SEQ ID NO:34), AQG, LAG, LQGV (SEQ ID NO:1), AQGV (SEQ ID NO:2), and LAGV (SEQ ID NO:10).

In a preferred embodiment, the invention provides the treatment of a subject suffering or believed to be suffering from inflammatory disease by mucosal, preferably oral administration of a pharmaceutical composition comprising a pharmacologically effective amount of a gene-regulatory peptide capable of regulating expression of genes encoding inflammatory mediators such as cytokines. Useful gene-regulatory peptides for inclusion in a pharmaceutical application for mucosal administration for the treatment of disease, in particular inflammatory disease are those peptides that are present naturally in pregnant women and are derived from proteolytic breakdown of placental gonadotropins such as human chorionic gonadotropin (hCG) produced during pregnancy, however, synthetic variants and modifications of these peptides that have functional equivalent or analogue activity can be synthesized and tested for their activity easily by the person skilled in the art, using, for example, animal experiments, such as experiments with NOD mice as explained herein. In another embodiment the invention provides a pharmaceutical composition for mucosal application comprising a gene-regulatory peptide or functional analogue thereof, and use of a gene-regulatory peptide or functional analogue thereof for the production of a pharmaceutical composition for mucosal application. Such a composition is most useful to apply to a mucosal surface area, the inner buccal surfaces and surfaces of the tongue, the surfaces of the (upper and lower) intestinal tract, the mucosal surfaces of the nose and (upper and lower) respiratory tract, and thereby, considering that in general the mucosal surfaces are permeable for most gene-regulatory peptides that are smaller than nine, but preferably smaller than seven amino acids, such as three or four amino acids long, often affects more than only the area to which it is applied, and is most useful to treat the body systemically, i.e., as a whole, as well.

The inventors have now unearthed an insight in the biology and physiology of the nature of regulatory factors in gene regulation in cellular organisms that allows for an unexpected fast progress in the identification and development of an artificial or synthetic compound acting as a gene regulator and its use as new chemical entity for the production of a pharmaceutical composition for mucosal application or its use in the treatment of inflammatory disease via the mucosal application of a gene-regulatory peptide. The insight is herein provided that many of small peptides that are derivable by proteolytic breakdown of endogenous proteins of an organism, or that are derivable by proteolytic breakdown of proteins of a pathogen, i.e., during the presence of the pathogen in a host organism, that exert an often very specific gene-regulatory activity on cells of the organism can actually exert this activity even on a systemic level when administered via mucosal uptake, such as by oral use, rectal application, nasal spray, upper airway aerosol application, and so on. In a particular embodiment, the present invention has major value for investigators in furthering the quality and quantity of knowledge regarding the systemic mechanisms controlling NFκB-initiated gene expression and resulting inflammatory responses in a subject by treatment of a subject with a pharmaceutical composition for mucosal application, for example, by oral use.

This insight was gained in a two fold way. In one experiment, designed to test the influence of mucosal uptake of gene-regulatory peptides, it was shown that NFκB-down-regulating peptides, instilled once daily in the buccal sac of non-diabetic NOD mice had an unexpected beneficial influence on the overall development of diabetes in these mice. The incidence of the development of the insulitis, the primary inflammation in the pathogenesis of diabetes, was severely reduced. In another experiment, already diabetic NOD mice were given drinking water with or without NFκB-down-regulating peptides, and also there a beneficial effect was observed, the clinical consequences of the typical secondary and systemic inflammation caused by the vascular damage were remarkably less severe, whereby the drinking water therapy contributed to a much better physical appearance of the treated versus the untreated group. Similar results were seen in mice treated mucosally or orally with a pharmaceutical composition comprising a functional analogue to a gene-regulatory peptide, a human chorionic gonadotropin (hCG) produced during pregnancy and proteolytic breakdown products thereof, however, batch wise differences in dose and effect were observed, likely reflecting batch wise differences in concentration of the regulatory peptides involved.

With these insights the invention provides among others a screening method for identifying or obtaining a gene-regulatory peptide suitable for mucosal or oral application comprising a peptide or functional derivative or analogue thereof capable of modulating expression of a gene in a cell, be it in vitro or in vivo in an experimentally diseased animal such as a monkey or a small laboratory animal such as a rat or mouse, comprising providing the animal via a mucosal route with at least one peptide or derivative or analogue thereof and determining the clinical response of the animal to the treatment or the expression of one or more genes in an animal or the activity and/or nuclear translocation of a gene transcription factor. It is in particular useful when the peptide is 3 to 15 amino acids long, more preferably, wherein the peptide is 3 to 9 amino acids long, most preferred wherein the peptide is 3 or 4 to 6 amino acids long.

Functional derivative or analogue herein relates to the gene-regulatory effect or activity as, for example, can be measured by measuring the peptide's or its analogue's or derivative's effect on gene expression or on nuclear translocation of a relevant transcription factor, such as NFκB in an NFκB assay, or AP-1 in an AP-1 assay, or by another method as is available in the art. Fragments can be somewhat (i.e., one or two amino acids) smaller or larger on one or both sides, while still providing functional activity.

A screening method according to the invention is also provided wherein the method further comprises determining whether the gene transcription factor regulates the transcription of a cytokine as, for example, measured by detecting cytokine transcript levels or the actual presence as such in the treated cell or animal, or wherein the gene transcription factor comprises an NFκB/Rel protein, or by determining relative up-regulation and/or down-regulation of at least one gene of interest expressed in the animal or of a multitude of genes expressed in the animal, as easily can be done with gene chip technology.

Of course, the invention aims at providing pharmaceutical compositions for mucosal application, such as oral use that act as a signaling molecule useful in modulating expression of a gene in a cell and are identifiable or obtainable by employing a screening method according to the invention as provided herein. Useful signaling molecules are already provided herein as modulators of NFκB/Rel protein-mediated gene-expression, as detailed further on. The invention also provides use of a signaling molecule as thus provided for the production of a pharmaceutical composition for the modulation of gene expression, for example, by inhibiting NFκB/Rel protein activation, or its use for the production of a pharmaceutical composition for the treatment of a primate or domestic animal.

That small peptides, and even breakdown products, can have biological activity, is already known. Proteolytic breakdown products of endogenous or pathogen-derived proteins are, for example, routinely generated by the proteasome system and presented in the context of class I or II major histocompatibility complex (MHC). Also, it has been recognized that classically known neuropeptides (also known as peptide neurotransmitters) or small peptide hormones, such as antidiuretic hormone, oxytocin, thyrotropin-releasing hormone, gonadotropin-releasing hormone, somatostatins gastrin, cholecystokinin, substance-P, enkephalins, neurotensin, angiotensins, and derivatives or equivalents thereof have distinct biological activity which is, in general, mediated by cell-surface receptor interaction. Furthermore, it is now known that certain small and arginine- or lysine- or proline-rich peptides, i.e., having more than 50% of arginine, or 50% of lysine or 50% of proline, or having more than 50% arginine and lysine, or more than 50% arginine and proline, or more than 50% lysine and proline, or more than 50% arginine and lysine and proline residues, have distinct membrane-permeation properties that may result in biological activity. The gene-regulatory peptides as used herein are other than the classically known neuropeptides or peptide hormones, and other than the above identified arginine- or lysine- or proline-rich peptides.

The present invention relates to small peptides suitable for mucosal application to treat disease systemically, in that the mucosal application has a systemic effect on a disease or condition in a subject treated via mucosal application with such a small peptide. Mucosal use and systemic effect of the gene-regulatory peptides is surprising. It is preferred that the peptides of the invention are small. A most preferred size is 4 to 6 amino acids, peptides of 2 to 3 amino acids are also very well feasible, a size of 7 to 15 amino acids is also feasible but becomes less practical for mucosal application and peptides from 10 to 15 amino acids or larger are preferably broken down to smaller, functionally more active, fragments.

As said, the invention provides the insight that small peptides that are derivable or obtainable by proteolytic breakdown of endogenous proteins of an organism, or that are derivable or obtainable by proteolytic breakdown of proteins of a pathogen, i.e., during the presence of the pathogen in a host organism, can exert an often very specific and systemic gene-regulatory activity on cells throughout the body of the organism, even after they have been applied only to a mucosal surface of the organism. This insight produces an immediate incentive for systematic approaches to practice or execute a method as provided herein to identify a signaling molecule, by obtaining information about the capacity or tendency of a small (oligo)peptide, or a modification or derivative thereof, (herein jointly called lead peptide) to systemically regulate expression of a gene after mucosal application and provides an incentive to try and test the chances of intradermal, transdermal, or hypodermal application.

The gene-regulatory peptide can be administered and introduced in-vivo preferably via any mucosal route, and possibly via passage through the skin. The peptide, or its modification or derivative, can be administered as the entity as such or as a pharmaceutically acceptable acid- or base-addition salt, formed by reaction with an inorganic acid (such as hydrochloric acid, hydrobromic acid, perchloric acid, nitric acid, thiocyanic acid, sulfuric acid, and phosphoric acid); or with an organic acid (such as formic acid, acetic acid, propionic acid, glycolic acid, lactic acid, pyruvic acid, oxalic acid, malonic acid, succinic acid, maleic acid, and fumaric acid); or by reaction with an inorganic base (such as sodium hydroxide, ammonium hydroxide, potassium hydroxide); or with an organic base (such as mono-, di-, trialkyl and aryl amines and substituted ethanolamines). A selected peptide and any of the derived entities may also be conjugated to DMSO, translocating peptides, sugars, lipids, other polypeptides, nucleic acids and PNA; and function in-situ as a conjugate or be released locally after reaching a targeted tissue or organ.

The invention also provides a pharmaceutical composition for the treatment of a subject suffering from a disease or disorder, the pharmaceutical composition comprising a pharmacologically effective amount of a gene-regulatory peptide together with a pharmaceutically acceptable diluent. In particular, the invention provides a pharmaceutical composition for mucosal application comprising a gene-regulatory peptide or functional analogue thereof, and use of a gene-regulatory peptide or functional analogue thereof for the production of a pharmaceutical composition for mucosal application. In a preferred embodiment, the invention provides a pharmaceutical composition for mucosal application comprising two or more gene-regulatory peptides or functional analogues thereof, and use of two or more gene-regulatory peptides or functional analogues thereof for the production of a pharmaceutical composition for mucosal application.

In one embodiment it is preferred that the pharmaceutical composition is in a form suitable for mucosal administration. In a much preferred embodiment, the form for mucosal administration is selected from the group consisting of sprays, liquids and gels, preferably with a watery base. In a much preferred embodiment, the invention provides a pharmaceutical composition for the treatment of a subject suffering from a disease or disorder, the pharmaceutical composition comprising a pharmacologically effective amount of a gene-regulatory peptide together with a pharmaceutically acceptable diluent wherein the pharmaceutical composition is in a form suitable for oral administration. It is preferred that the form for oral administration is selected from the group consisting of capsules, tablets, liquids, oral suspensions, emulsions and powders.

Although the gene-regulatory peptide may be prepared by other methods known for the preparation of analogous compounds (e.g., by use of a solid phase synthesis), a method of making the gene-regulatory peptide is described in the detailed description herein. During the process of preparation, solvents such as N,N-dimethylformamide (DMF), 1-butanol, 2-butanol, ethanol, methanol, ethyl acetate, methylene chloride, hexane, diethyl ether, water, acetic acid, and others may be used. Catalysts containing palladium or molybdenum may also be used in the preparation of the gene-regulatory peptide.

However made, the gene-regulatory peptide forms pharmacologically acceptable salts from pharmacologically acceptable organic and inorganic acids such as hydrochloric, hydrobromic, fumaric, phosphoric, ascorbic, tartaric, citric, lactic, maleic, palmitic, and other well-known acids. Especially preferred are the hydrochloric and acetic acid salts. The acid addition salts are obtained by reacting the gene-regulatory peptide with the acid.

Methods of crystallizing compounds are described in Chase et al., *Remington's Pharmaceutical Sciences* (16th ed., Mack Publishing Co., Easton. Pa., U.S.A., 1980) ("Remington's"), at page 1535.

A crystalline gene-regulatory peptide can be used to make numerous dosage forms such as powders for insufflations, powders for reconstitution, tablet triturates (e.g., dispensing tablets and hypodermic tablets), other tablets, and so forth.

The pharmaceutical compositions containing the crystalline gene-regulatory peptide are preferably dispensed in unit dosage forms, such as tablets, capsules, pills, powders, granules, suppositories, sterile parenteral solutions or suspensions and non-parenteral solutions or suspensions, containing suitable quantities of the pharmaceutically acceptable salt of the gene-regulatory peptide.

Methods and compositions for making such dosage forms are well-known to those skilled in the art. For example, methods of making powders and their compositions are described at pages 1535 through 1552 of Remington's. Insufflations are described at page 1552, and insufflators are described at 1792. Methods and compositions for making tablets and pills, containing active ingredients, are described in Remington's, at pages 1553 through 1584. Methods of coating pharmaceutical dosage forms and making prolonged release pharmaceuticals are described at pages 1585-1613 of Remington's. The contents of these pages are hereby incorporated by this reference.

The crystalline gene-regulatory peptide may also be incorporated into devices intended for implantation into a patient. Such devices, polymers intended for use therein, and methods of making both are described in U.S. Pat. Nos. 3,773,919, 4,767,628, and 4,675,189. For example, a sufficient quantity of the crystalline gene-regulatory peptide could be incorporated into a PLAGA implant to allow for the release of gene-regulatory peptide (e.g., 5 mg per day for one month) into the patient's body.

One advantage with pharmaceutical compositions containing the crystalline versus the amorphous product, is that the pharmaceutical composition containing the crystalline salt product, having twice the bioavailability of the amorphous product, may need only contain half the absolute amount of the active ingredient on certain mucosa thus decreasing the amount of ingredient needed to be insufflated or otherwise administered and decreasing the ultimate cost of the composition. Such mucosa would include the nasal and the buccal mucosa.

Although the pharmaceutical compositions containing the crystalline gene-regulatory peptide may be formulated with adjuvants such as solubilizers, they need not be. The ability to use solely the crystalline gene-regulatory peptide (i.e., the crystalline acid addition salt of the gene-regulatory peptide) in a pharmaceutical composition to be applied to, for example, a nasal mucosa has advantages. For one thing, certain adjuvants are not suitable for chronic administration. However, long term administration may be necessary for the particular person ingesting the gene-regulatory peptide. Another advantage is that the adjuvants necessarily take up a portion of the pharmaceutical composition, which portion may be better suited for the gene-regulatory peptide in order to decrease mucosal discomfort.

However if it is desired, suitable solubilizers, buffers, swelling agents, etc. may be used in such formulations. Buffering agents are preferably those which keep the gene-regulatory peptide in its unionized form.

The dosage of the crystalline acid addition salt/gene-regulatory peptide administered will generally be dependent upon the kind of disorder to be treated, the type of patient involved, his age, health, weight, kind of concurrent treatment, if any, and length and frequency of treatment.

The dosage forms will be administered over varying durations. To treat a disorder, the compounds are administered to a patient for a length of time sufficient to alleviate the symptoms associated with the disorders that the patient is suffering from. This time will vary, but periods of time exceeding two months are especially preferred. After the symptoms have been alleviated, the compound may then be discontinued to determine whether it is still required by the particular patient.

To prevent the occurrence of inflammatory disease, and thus alleviate the need for treatment, the compounds are administered to a person believed to be susceptible to suffering from inflammatory disease some time in the future (e.g., patients undergoing treatment with cytotoxic drugs such as vincristine; diabetics; alcoholics; etc.) for so long as he or she is believed susceptible. The length of such prophylactic administration of the compounds will of course vary, but again, periods of time exceeding two months are preferred. If the reason for the supposed susceptibility to an inflammatory disease has ceased to exist, the compound may then be discontinued. If however the reason for the disorder has not ceased to exist (e.g., in the case of diabetes) the compound may be needed to be administered for the person's lifetime.

Illustratively, dosage levels of the administered active ingredients can be (intranasally): between 0.55 mg and 270 mg per day. In human therapy, daily doses of between 8 mg and 120 mg, administered orally, will preferably be used.

The invention provides a pharmaceutical composition for oral application comprising a gene-regulatory peptide or functional analogue thereof, and use of a gene-regulatory peptide or functional analogue thereof for the production of a pharmaceutical composition for oral application. In a preferred embodiment, the invention provides a pharmaceutical composition for oral application comprising two or more gene-regulatory peptides or functional analogues thereof, and use of two or more gene-regulatory peptides or functional analogues thereof for the production of a pharmaceutical composition for oral application.

The gene-regulatory peptide(s) is (are) incorporated into dosage units for oral administration. The term "dosage unit" generally refers to physically discrete units suitable as unitary dosages for humans or animals, each containing a predetermined quantity of active material (e.g., gene-regulatory peptide) calculated to produce the desired effect.

Methods and compositions for making such dosage units are well-known to those skilled in the art. For example, methods and compositions for making tablets and pills, containing active ingredients, are described in the standard reference, Chase et al., *Remington's Pharmaceutical Sciences* (16th ed., Mack Publishing Co., Easton, Pa., U.S.A., 1980) ("Remington's"), at pages 1553 to 1584. Methods of making powders, and their composition are described at pages 1535 to 1552 of the reference. Methods of coating pharmaceutical dosage forms are described at pages 1585 to 1593 of Remington's.

For making dosage units, e.g., tablets, the use of conventional additives, e.g., fillers, colorants, polymeric binders and the like is contemplated. In general any pharmaceutically acceptable additive which does not interfere with the function of the active compounds can be used in the one or more of the compositions.

Suitable carriers with which the compositions can be administered include lactose, starch, cellulose derivatives and the like used in suitable amounts. Lactose is a preferred carrier. Mixtures of carriers can also be used.

A process of manufacturing the pharmaceutical composition for oral use involves mixing predetermined quantities of peptide with predetermined quantities carrier and converting the mixture into the first dosage units (e.g., by filling capsules or molding tablets with the mixture and any desired excipients)

A preferred process of manufacturing the gene-regulatory product according to the invention involves incorporating the desired dosages of gene-regulatory peptide into a tablet by known techniques. Tablets or other dosage units containing different amounts and types of gene-regulatory peptides may be of different colors, and kept in different portions of, for example, a blister pack.

In another embodiment, the invention provides a pharmaceutical composition for rectal application, such as a suppository comprising a gene-regulatory peptide or functional analogue thereof, and use of a gene-regulatory peptide or functional analogue thereof for the production of a pharmaceutical composition for rectal application.

In another embodiment, the invention provides a pharmaceutical composition for sub- or transdermal application comprising a gene-regulatory peptide or functional analogue thereof, and use of a gene-regulatory peptide or functional analogue thereof for the production of a pharmaceutical composition for sub- or transdermal application.

A pharmaceutical composition for mucosal application or application via the skin as provided herein is particularly useful for the modulation of gene expression by inhibiting NFκB/Rel protein-mediated cytokine activation.

NFκB/Rel proteins are a group of structurally related and evolutionarily conserved proteins (Rel). Well known are c-Rel, RelA (p65), RelB, NFκB1 (p50 and its precursor p105), and NFκB2 (p52 and its precursor p100). Most NFκB dimers are activators of transcription; p50/p50 and p52/p52 homodimers repress the transcription of their target genes. All NFκB/Rel proteins share a highly conserved NH2-terminal Rel homology domain (RHD). RHD is responsible for DNA binding, dimerization, and association with inhibitory proteins known as IκBs. In resting cells, NFκB/Rel dimers are bound to IκBs and retained in an inactive form in the cytoplasm. IκBs are members of a multigene family (IκBα, IκBβ, IκBγ, IκBepsilon, Bcl-3, and the precursor Rel-proteins, p100 and p105. Presence of multiple copies of ankyrin repeats interact with NFκB via the RHD (protein-protein interaction. Upon appropriate stimulation, IκB is phosphorylated by IκB Kinase (IKKs), polyubiquitinated by ubiquitin ligase complex, and degraded by the 26S proteosome. NFκB is released and translocates into nucleus to initiate gene expression.

NFκB regulation of gene expression includes innate immune responses: such as regulated by cytokines IL-1, IL-2, IL-6, IL-12, TNF-α, LT-α, LT-β, GM-CSF; expression of adhesion molecules (ICAM, VCAM, endothelial leukocyte adhesion molecule [ELAM]), acute phase proteins (SAA), inducible enzymes (iNOS and COX-2) and antimicrobial peptides (β-defensins). For adaptive immunity, MHC proteins IL-2, IL-12 and IFN-α are regulated by NFκB. Regulation of overall immune response includes the regulation of genes critical for regulation of apoptosis (c-IAP-1 and c-IAP-2, Fas Ligand, c-myc, p53 and cyclin D1.

Considering that NFκB and related transcription factors are cardinal pro-inflammatory transcription factors, and considering that the invention provides a gene-regulatory peptide and functional analogue or derivative suitable for mucosal application that is capable of systemically inhibiting NFκB and likely also other pro-inflammatory transcription factors, herein also called NFκB inhibitors, the invention provides a method and pharmaceutical composition for systemically modulating NFκB activated gene expression, in particular for inhibiting the expression and thus inhibiting a central pro-inflammatory pathway. In a preferred embodiment, the gene-regulatory peptide is administered orally, to exert its activity systemically, beyond the mucosal surface to which it is applied.

The consequence of this potency to inhibit this pro-inflammatory pathway systemically via a mucosal, such as an oral application, is wide and far-reaching.

For one, a novel therapeutic inroad is provided using the pharmaceutical potential of gene-regulatory peptides and derivatives applied mucosally or orally for generating a systemic response directed at modulating NKκB-mediated disease. Earlier, we presented evidence of specific up- or down-regulation of NFκB driven pro- or anti-inflammatory cytokine cascades that are each, and in concert, directing the body's immune response was found in silico in gene-arrays by expression profiling studies, in vitro after treatment of immune cells and in vivo in experimental animals treated with gene-regulatory peptides. Also, considering that NFκB is a primary effector of disease, using the hCG-derived gene-regulatory peptides via an oral or otherwise mucosal application offers significant potential for the treatment of a variety of human and animal diseases, thereby tapping the systemic pharmaceutical potential of the exact substances that help balance the mother's immune system such that her pregnancy is safely maintained by applying a gene-regulatory peptide mucosally, preferably orally.

Examples of NFκB-modulated disease are foremost found among the earlier discussed inflammatory conditions.

Conditions that can be treated orally with a pharmaceutical composition as provided herein preferably include subacute or chronic inflammatory disease, such as diabetes type I or II, rheumatic disease, Sjögrens syndrome, multiple sclerosis), transplantation-related immune responses such as graft-versus-host-disease, post-transfusion thrombocytopenia, subacute and chronic transplant rejection, pre-eclampsia, rheumatoid arthritis, inflammatory bowel disease, the inflammatory component of neurological or psychiatric disorders, atherosclerosis, asthma, allergy and chronic auto-immune disease. Especially the oral treatment of systemic autoimmune disease will be very helpful in the treatment of patients with chronic, immune-mediated inflammation, as is the case in autoimmune disease. A non-limiting list of thus treatable autoimmune diseases includes: Hashimoto's thyroditis, primary mysxoedema thyrotoxicosis, pernicious anemia, autoimmune atrophic gastritis, Addison's disease, premature menopause, insulin-dependent diabetes mellitus, stiff-man syndrome, Goodpasture's syndrome, myasthenia gravis, male infertility, pemphigus vulgaris, pemphigoid, sympathetic ophthalmia, phacogenic uveitis, multiple sclerosis, autoimmune hemolytic anemia, idiopathic thrombocytopenic purpura, idiopathic leucopenia, primary biliary cirrhosis, active chronic hepatitis, cryptogenic cirrhosis, ulcerative colitis, Sjögren's syndrome, rheumatoid arthritis, dermatomyositis, polymyositis, scleroderma, mixed connective tissue disease, discoid lupus erythematosus, and systemic lupus erythematosus.

The invention thus also relates to the treatment of the inflammatory component of neurological disorders or so called neuroimmune disorders such as schizophrenia, manic depression and other bipolar disorders, post-partum psychosis and autism. The invention provides a method for modulating a neurological disorder in a subject comprising providing the subject with a gene-regulatory peptide or functional analogue thereof. The invention also provides use of an NFκB down-regulating peptide or functional analogue thereof for the production of a pharmaceutical composition for the treatment of a neurological disorder.

The invention provides a method for modulating a neurological disorder in a subject comprising providing the subject orally with a gene-regulatory peptide or functional analogue thereof, in particular wherein the regulatory peptide down-regulates translocation and/or activity of a gene transcription factor, such as an NFκB/Rel protein. Preferred peptides for modulating a neurological disorder by oral treatment are LQG, QVV, PALP (SEQ ID NO:34), AQG, LAG, LQGV (SEQ ID NO:1), AQGV (SEQ ID NO:2), or LAGV (SEQ ID NO:10). The peptides are also useful for the production of a pharmaceutical composition for the treatment of a neurological disorder, especially wherein the peptide or analogue is selected from the group of peptides analogues having NFκB down-regulating activity in LPS-stimulated RAW264.7 cells or in LPS-unstimulated RAW264.7 cells.

The invention also relates to the oral treatment of multiple sclerosis, and in particular to the treatment of the inflammatory injury seen in the progressive stages in the disease such as seen with the recurrent upsurges of acute disease, classically known as relapses or exacerbations herein identified as relapsing/remitting disease seen in multiple sclerosis. The invention provides a method for modulating relapsing/remitting disease as seen with multiple sclerosis in a subject comprising providing the subject orally with a gene-regulatory peptide or functional analogue thereof.

The invention in particular provides a method for modulating relapsing/remitting disease as seen in multiple sclerosis in a subject comprising orally providing the subject with a gene-regulatory peptide or functional analogue thereof, in particular wherein the gene-regulatory peptide down-regulates translocation and/or activity of a gene transcription factor, preferably wherein the gene transcription factor comprises an NFκB/Rel protein of which translocation and/or activity is inhibited It is preferred to orally administer such a peptide, preferably selected from the group of LQG, QVV, PALP (SEQ ID NO:34), AQG, LAG, LQGV (SEQ ID NO:1), AQGV (SEQ ID NO:2), LAGV (SEQ ID NO:10), when the subject is presenting clinical signs of exacerbations.

The invention also provides use of such an NFκB down-regulating peptide or functional analogue thereof for the production of a pharmaceutical composition for the treatment of relapsing/remitting disease as seen with multiple sclerosis.

The invention, thus, also relates to the treatment of diabetes. The invention provides a method for modulating diabetes in a subject comprising providing the subject orally with a gene-regulatory peptide or functional analogue thereof. The invention also provides use of an NFκB down-regulating peptide or functional analogue thereof for the production of a pharmaceutical composition for the oral treatment of diabetes.

The invention provides a method for modulating diabetes in a subject comprising providing the subject orally with a gene-regulatory peptide or functional analogue thereof, in particular wherein the regulatory peptide down-regulates translocation and/or activity of a gene transcription factor, such as an NFκB/Rel protein. Preferred peptides for modulating diabetes by oral treatment are LQG, QVV, PALP (SEQ ID NO:34), AQG, LAG, LQGV (SEQ ID NO:1), AQGV (SEQ ID NO:2), or LAGV (SEQ ID NO:10). The peptides are also useful for the production of a pharmaceutical composition for the treatment of diabetes by oral administration, especially wherein the peptide or analogue is selected from the group of peptides analogues having NFκB down-regulating activity in LPS-stimulated RAW264.7 cells or in LPS-unstimulated RAW264.7 cells.

The invention also provides a method of treatment of a menopausal condition or a post-menopausal condition, such as osteoporosis, comprising oral or mucosal treatment with a gene-regulatory peptide according to the invention allowing systemic modulation and inhibition of osteoclast differentiation and inhibiting TNF-α-induced apoptosis of osteoblasts, thereby limiting the dissolve of bone structures, otherwise so prominent in post-menopausal women that have no longer a natural source of hCG and thus lack the modulatory effect of the signal molecules that are derived of hCG as shown herein. The invention thus also provides a method of mucosal or oral treatment of a bone disease, such as osteoporosis (which is often, but not exclusively, seen with post-menopausal women). Furthermore, NO and TNF-α modulators as provided herein inhibit the inflammatory response and bone loss in periodontitis. Furthermore, considering that there is a correlation between TNF-α activity and severity of clinical manifestations in ankylosing spondylitis, the invention provides the treatment of spondylitis by use of a gene-regulatory peptide as provided herein. Preferred peptides for modulating a menopausal, post-menopausal or osteoporosis condition by oral treatment are QVV, PALP (SEQ ID NO:34), AQG, LAG, LQGV (SEQ ID NO:1), AQGV (SEQ ID NO:2), or LAGV (SEQ ID NO:10).

The invention also relates to the oral or mucosal treatment of an ischemic event such as a stroke or myocardial infarction.

An ischemic event refers to an event in which the blood supply to a tissue is obstructed. Due to this obstruction, the endothelial tissue lining the affected blood vessels becomes "sticky" and begins to attract circulating white blood cells. The white cells bound to the endothelium eventually migrate into the affected tissue, causing significant tissue destruction. Although neither acute myocardial infarction nor stroke is directly caused by inflammation, much of the underlying pathology and the damage that occurs after an acute ischemic event are caused by acute inflammatory responses during reperfusion, the restoration of blood flow to the affected organ. Early restitution of blood flow to ischemic tissues is essential to halt the progression of cellular injury associated with decrease of oxygen supply and nutrient delivery. This fact provides the basis for the traditional view that minimizing ischemic time is the only important intervention for diminishing the extent of ischemic injury. However, it is now well recognized that reperfusion of ischemic tissues initiates a complex series of reactions that can paradoxically injure tissues. Although several mechanisms have been proposed to explain the pathogenesis of ischemia—reperfusion injury, most attention has focused on a role for reactive oxygen and nitrogen metabolites and inflammatory leukocytes. In addition to the local tissue injury, distant organs can also be affected, particularly if the intensity of the inflammatory reaction in postischemic tissue (e.g., intestine) is great. The remote effects of ischemia—reperfusion injury are most frequently observed in the lung and (cardio- or cerebro-) vascular system, and can result in the development of the systemic inflammatory response syndrome (SIRS) and multiple organ dysfuntion syndrome (MODS), both of which account for 30 to 40% of the mortality in tertiary referral intensive care units (ICUs).

The invention provides a method for modulating or treating such an ischemic event in a subject comprising providing the subject with orally or mucosally with a gene-regulatory peptide or functional analogue thereof, in particular wherein the peptide down-regulates translocation and/or activity of a gene transcription factor, preferably wherein the gene transcription factor comprises an NFκB/Rel protein an wherein translocation and/or activity of the NFκB/Rel protein is inhibited. For mucosal or oral application it is preferred that the peptide is selected from the group of peptides having NFκB down-regulating activity in LPS-stimulated RAW264.7 cells, especially when the subject is at risk to experience reperfusion injury occurring after the ischemic event.

For achieving a rapid clinical intervention by oral or mucosal administration it is preferred that the peptide is selected from the group of peptides having NFκB down-regulating activity in LPS-unstimulated RAW264.7 cells, then the subject may also provided with a thrombolytic agent, such as when the thrombolytic agent comprises tissue plasminogen activity.

Furthermore, the invention provides use of a gene-regulatory peptide, preferably comprising an NFκB down-regulating peptide or functional analogue thereof, for the production of a pharmaceutical composition for the oral or mucosal treatment of reperfusion injury occurring after an ischemic event in a subject. The most preferred peptide for treating such as reperfusion injury orally is AQGV (SEQ ID NO:2).

The invention furthermore relates to the oral or mucosal treatment of immunosuppressive effects such as those seen after trauma or major surgery. In the United States, posttraumatic sepsis is responsible for 60% of all late deaths after trauma. The susceptibility of trauma patients to sepsis seems to be caused at least in part by a profound suppression of cellular immunity often found after trauma, burns and hemorrhage. The relationship between the nervous and the immune system following trauma or other life-threatening events is poorly understood and under investigation. Recent reviews have highlighted the complex nature of the tremendous surge of hormone and catecholamine output from the pituitary-adrenal axis following trauma, which may be mediated through the spinal cord along afferent neurons from the site of tissue destruction. Also, often a generalized depression of the immune system exists. The invention provides a method for oral or mucosal treatment of an immunosuppressive state in a subject comprising providing the subject via oral or mucosal application with a gene-regulatory peptide or functional analogue thereof. Such treatment is particularly useful when the subject has experienced trauma or major surgery likely resulting in an immunosuppressive state. It is preferred that the peptide or analogue up-regulates translocation and/or activity of a gene transcription factor such as an NFκB/Rel protein AP-1 protein. In a much preferred embodiment, the peptide is selected from the group of peptides having NFκB up-regulating activity in LPS-unstimulated RAW264.7 cells; such treatment is also very useful when the subject is at risk to experience a counter anti-inflammatory response syndrome, especially when the peptide is selected from the group of peptides having NFκB up-regulating activity in LPS-stimulated RAW264.7 cells. Further therapy may include providing the subject with an agent directed against disseminated intravascular coagulation, such as when the agent comprises Activated Protein C activity. Also, the invention provides use of a gene-regulatory peptide, in particular an NFκB up-regulating peptide or functional analogue thereof for the production of a pharmaceutical composition for the oral or mucosal treatment of an immunosuppressive state or a counter anti-inflammatory response syndrome in a subject.

The invention also relates to the field of (veterinary) medicine and to the oral or mucosal treatment of subjects (be it man or animal) that suffer from iatrogenic disease, i.e., experience problems or complications resulting from a medical treatment. Iatrogenic events that result from activities of, for example, physicians or surgeons are commonplace in modem medicine and can often not be avoided. Various adverse conditions can occur due to malpractice or neglect, such as wrongly selecting or executing a therapy, misplacing or forgetting to remove surgical utensils during surgery, and the like. However, most therapeutic or surgical interventions, even those well selected and properly executed, may, even beyond their beneficial effects, cause adverse and often inflammatory conditions in a patient. Furthermore, also tried and tested therapies in infectious disease, such as treatments with antibiotics or antivirals, have their iatrogenic side-effects, often related to the lysis or destruction of the very micro-organism they are designed to be used against, and the release of microbe membrane fragments and/or toxins which induces additional pro-inflammatory cytokine release. Whatever the cause may be, most iatrogenic events, herein defined as a disorder or disease resulting from a treatment of a human or animal subject with a pharmaceutical composition or by a medical or surgical procedure, result in the damage, destruction or lysis of cells or tissue of the subject, resulting in additional pro-inflammatory cytokine release.

The invention provides a method for treating an iatrogenic event in a subject comprising providing the subject orally or mucosally with a gene-regulatory peptide or functional analogue thereof, particularly when the peptide modulates translocation and/or activity of a gene transcription factor such as an NFκB/Rel protein or causes inhibition of an NFκB/Rel protein-mediated cytokine gene expression. It is very useful to treat a subject orally or mucosally when the iatrogenic event comprises destruction or lysis of a cell or tissue of the subject or of a pathogen hosted by the subject, for example, when the lysis is due to treatment of the subject with a pharmaceutical composition, such as a pharmaceutical composition that is selected from the group of antigens, vaccines, antibodies, anticoagulants, antibiotics, antitoxins, antibacterial agents, antiparasitic agents, antiprotozootic agents, antifungal agents, antiviral agents, cytolytic agents, cytostatic agents, thrombolytic agents. Such treatment is also useful when the lysis is due to treatment of the subject with a virus, such as a lytic phage. The invention also provides use of a signaling molecule comprising an NFκB down-regulating peptide or functional analogue thereof for the production of a pharmaceutical composition for the oral or mucosal treatment of a pro-inflammatory cytokine response occurring after an iatrogenic event in a subject.

Other examples of disease or disorders that can be treated mucosally or orally with a pharmaceutical composition as provided herein include acute inflammatory disease, such as (hyper)acute transplant rejection, sepsis/SIRS, for example, after burn injury and acute autoimmune disease.

In particular, the invention provides oral or mucosal treatment of an acute systemic disease such as sepsis/SIRS. Sepsis/SIRS is an acute systemic inflammatory response to a variety of noxious insults (particularly insults of an infectious origin such as a bacterial infection, but also non-infectious insults are well known and often seen). The systemic inflammatory response seen with sepsis/SIRS is caused by immunological processes that are activated by a variety of immunological mediators such as cytokines, chemokines, nitric oxide, and other immune mediating chemicals of the body. These immunological mediators are generally seen to cause the life-threatening systemic disease seen with sepsis/SIRS.

The invention provides a method for treating sepsis/SIRS in a subject comprising providing the subject orally or mucosally with a gene-regulatory peptide or functional analogue thereof, particularly when the peptide modulates translocation and/or activity of a gene transcription factor such as an NFκB/Rel protein or causes inhibition of an NFκB/Rel protein-mediated cytokine gene expression. It is very useful to treat a subject orally or mucosally when the sepsis/SIRS finds its basis in the ongoing destruction or lysis of a cell or tissue of the subject or of a pathogen hosted by the subject. The invention also provides use of a gene-regulatory peptide, in particular of an NFκB down-regulating peptide or functional analogue thereof for the production of a pharmaceutical composition for the treatment of a systemic inflammatory response syndrome or sepsis of a subject.

The gene-regulatory activity of a gene-regulatory peptide, in particular of an NFκB-regulating peptide such as selected from the group of peptides LQG, AQG, LQGV (SEQ ID NO:1), AQGV (SEQ ID NO:2), LQGA (SEQ ID NO:3), VLPALP (SEQ ID NO:4), ALPALP (SEQ ID NO:5), VAPALP (SEQ ID NO:6), ALPALPQ (SEQ ID NO:7), VLPAAPQ (SEQ ID NO:8), VLPALAQ (SEQ ID NO:9), LAGV (SEQ ID NO:10), VLAALP (SEQ ID NO:11), VLAALP (SEQ ID NO:11), VLPALA (SEQ ID NO:12), VLPALPQ (SEQ ID NO:13), VLAALPQ (SEQ ID NO:14), VLPALPA (SEQ ID NO:15), GVLPALP (SEQ ID NO:16), LQGVLPALPQVVC (SEQ ID NO:17), LPGCPRGVNPVVS (SEQ ID NO:18), LPGC (SEQ ID NO:19), MTRV (SEQ ID NO:20), MTR, VVC is manifested in the following way. Classically, many genes are regulated not by a signaling molecule that enters the cells but by molecules that bind to specific receptors on the surface of cells. Interaction between cell-surface receptors and their ligands can be followed by a cascade of intracellular events including variations in the intracellular levels of so-called second messengers (diacylglycerol, $Ca^{2+}$, cyclic nucleotides). The second messengers in turn lead to changes in protein phosphorylation through the action of cyclic AMP, cyclic GMP, calcium-activated protein kinases, or protein kinase C, which is activated by diaglycerol. Many of these classic responses to binding of ligands to cell-surface receptors are cytoplasmatic and do not involve immediate gene activation in the nucleus. Some receptor-ligand interactions, however, are known to cause prompt nuclear transcriptional activation of a specific and limited set of genes. However, progress has been slow in determining exactly how such activation is achieved. In a few cases, the transcriptional proteins that respond to cell-surface signals have been characterized.

One of the clearest examples of activation of a pre-existing inactive transcription factor following a cell-surface interaction is the nuclear factor (NF)κB, which was originally detected because it stimulates the transcription of genes encoding immunoglobulin light chains of the κ class in B-lymphocytes. The binding site for NKκB in the κ gene is well defined (see, for example, P. A. Baeuerle and D. Baltimore, 1988, *Science* 242:540), providing an assay for the presence of the active factor. This factor exists in the cytoplasm of lymphocytes complexed with an inhibitor. Treatment of the isolated complex in vitro with mild denaturing conditions dissociates the complex, thus freeing NKκB to bind to its DNA site. Release of active NFκB in cells is now known to occur after a variety of stimuli including treating cells with bacterial lipopolysaccharide (LPS) and extracellular polypeptides as well as chemical molecules (e.g., phobol esters) that stimulate intracellular phosphokinases. Thus a phosphorylation event triggered by many possible stimuli may account for NFκB conversion to the active state. The active factor is then translocated to the cell nucleus to stimulate transcription only of genes with a binding site for active NFκB. We have found that a variety of short peptides as indicated above exert a modulatory activity on NFκB activity.

Considering that the inflammatory response involves the sequential release of mediators and the recruitment of circulating leukocytes, which become activated at the inflammatory site and release further mediators (*Nat. Med.* 7:1294; 2001), we provided using NFκB-regulating peptide in the field medicine, e.g., by providing pharmaceutical compositions and methods for use in the medicine. Considering that NFκB is thought by many to be a primary effector of disease (A. S. Baldwin, *J. Clin. Invest.*, 2001, 107:3-6), numerous efforts are underway to develop safe inhibitors of NFκB to be used in treatment of both chronic and acute disease situations.

For example, concomitantly or separately with a method for perfusing a transplant with a perfusing fluid, the invention herewith provides treating the recipient of the transplant with a pharmaceutical composition for oral or mucosal use comprising at least one gene-regulatory peptide, preferably an NFκB down-regulating peptides as provided herein; ischemic or post-implantation damage due to activation of NFκB in the transplant and/or the recipient can then be greatly diminished, allowing a longer survival and use of the transplants. It is now provided that the use also allows reducing the risk on chronic transplant rejection, allowing increasing transplant survival. The invention provides a method for avoiding acute and in particular chronic rejection of a transplant and increasing transplant survival in a recipient of the transplant comprising providing the recipient orally or mucosally with a gene-regulatory peptide or functional analogue thereof, herein also called a signaling molecule. It is preferred that the peptide is 3 to 15 amino acids long, more preferably, that the peptide is 3 to 9 amino acids long, it most preferred that the peptide is 4 to 6 amino acids long. It is in particular preferred that the signaling molecule is capable of inhibiting NFκB/Rel protein activity.

Functional analogue herein relates to the signaling molecular effect or activity as, for example, can be measured by measuring nuclear translocation of a relevant transcription factor, such as NFκB in an NFκB assay, or AP-1 in an AP-1 assay, or by another method as provided herein. Fragments can be somewhat (i.e., one or two amino acids) smaller or larger on one or both sides, while still providing functional activity. In one embodiment of the invention, the peptide used as a signaling molecule or gene-regulatory peptide is a chemically modified peptide. A peptide modification includes phosphorylation (e.g., on a Tyr, Ser or Thr residue), N-terminal acetylation, C-terminal amidation, C-terminal hydrazide, C-terminal methyl ester, fatty acid attachment, sulfonation (tyrosine), N-terminal dansylation, N-terminal succinylation, tripalmitoyl-S-Glyceryl Cysteine (PAM3 Cys-OH) as well as farnesylation of a Cys residue. Systematic chemical modification of a peptide can, for example, be performed in the process of peptide optimalization.

Synthetic peptides can be obtained using various procedures known in the art. These include solid phase peptide synthesis (SPPS) and solution phase organic synthesis (SPOS) technologies. SPPS is a quick and easy approach to synthesize peptides and small proteins. The C-terminal amino acid is typically attached to a cross-linked polystyrene resin via an acid labile bond with a linker molecule. This resin is insoluble in the solvents used for synthesis, making it relatively simple and fast to wash away excess reagents and by-products. The peptide, or its functional analogue, modification or derivative, can be administered as the entity as such or as a pharmaceutically acceptable acid- or base-addition salt, formed by reaction with an inorganic acid (such as hydrochloric acid, hydrobromic acid, perchloric acid, nitric acid, thiocyanic acid, sulfuric acid, and phosphoric acid); or with an organic acid (such as formic acid, acetic acid, propionic acid, glycolic acid, lactic acid, pyruvic acid, oxalic acid, malonic acid, succinic acid, maleic acid, and fumaric acid); or by reaction with an inorganic base (such as sodium hydroxide, ammonium hydroxide, potassium hydroxide); or with an organic base (such as mono-, di-, trialkyl and aryl amines and substituted ethanolamines). A selected peptide and any of the derived entities may also be conjugated to sugars, lipids, other polypeptides, nucleic acids and PNA; and function in-situ as a conjugate or be released locally after reaching a targeted tissue or organ.

In response to a variety of pathophysiological and developmental signals, the NFκB/Rel family of transcription factors are activated and form different types of hetero- and homodimers among themselves to regulate the expression of target genes containing κB-specific binding sites. NFκB transcription factors are hetero- or homodimers of a family of related proteins characterized by the Rel homology domain. They form two subfamilies, those containing activation domains (p65-RELA, RELB, and c-REL) and those lacking activation domains (p50, p52). The prototypical NFκB is a heterodimer of p65 (RELA) and p50 (NFκB1). Among the activated NFκB dimers, p50-p65 heterodimers are known to be involved in enhancing the transcription of target genes and p50-p5O homodimers in transcriptional repression. However, p65-p65 homodimers are known for both transcriptional activation and repressive activity against target genes. κB DNA-binding sites with varied affinities to different NFB dimers have been discovered in the promoters of several eukaryotic genes and the balance between activated NFκB homo- and heterodimers ultimately determines the nature and level of gene expression within the cell. The term "NFκB-regulating peptide" as used herein refers to a peptide or functional analogue or a modification or derivative thereof capable of modulating the activation of members of the NFκB/Rel family of transcription factors. Examples of such peptides that are particularly useful in a method or composition according to the invention are selected from the group of VLPALPQVVC (SEQ ID NO:21), LQGVLPALPQ (SEQ ID NO:22), LQGV (SEQ ID NO:1), AQGV (SEQ ID NO:2), GVLPALPQ (SEQ ID NO:23), VLPALP (SEQ ID NO:4), VLPALPQ (SEQ ID NO:13), GVLPALP (SEQ ID NO:16), VVC, MTRV (SEQ ID NO:20), and MTR. Modulation of the activation of NFκB can lead to enhanced transcription of target genes. Also, it can lead to transcriptional repression of target genes. NFκB activation can be regulated at multiple levels. For example, the dynamic shuttling of the inactive NFκB dimers between the cytoplasm and nucleus by IκB proteins and its termination by phosphorylation and proteasomal degradation, direct phosphorylation, acetylation of NFκB factors, and dynamic reorganization of NFκB subunits among the activated NFκB dimers have all been identified as key regulatory steps in NFκB activation and, consequently, in NFκB-mediated transcription processes. Thus, an NFκB-regulating peptide is capable of modulating the transcription of genes that are under the control of NFκB/Rel family of transcription factors. Modulating comprises the up-regulation or the down-regulation of transcription.

The term "pharmaceutical composition" as used herein is intended to cover both the active regulatory peptide or analogue alone or a composition containing the regulatory peptide or analogue together with a pharmaceutically acceptable carrier, diluent or excipient. Acceptable diluents of a peptide are, for example, physiological salt solutions or phosphate buffered salt solutions. It is in particular useful to provide a pharmaceutical composition wherein the gene transcription factor comprises an NFκB/Rel protein. For example, to counter ischemia-reperfusion damage of a transplant, for example, derived from a brain dead donor or, to prevent ischemia-reperfusion damage during cold storage and transport of a transplant, it is herein recommended to provide a pharmaceutical composition by which translocation and/or activity of the NFκB/Rel protein is inhibited. Such a composition can be a transplant preservation or perfusion fluid as described herein, comprising a gene-regulatory peptide or functional analogue thereof. It is useful to select the peptide from the group of peptides LQG, AQG, LQGV (SEQ ID NO:1), AQGV (SEQ ID NO:2), LQGA (SEQ ID NO:3), VLPALP (SEQ ID NO:4), ALPALP (SEQ ID NO:5), VAPALP (SEQ ID NO:6), ALPALPQ (SEQ ID NO:7), VLPAAPQ (SEQ ID NO:8), VLPALAQ (SEQ ID NO:9), LAGV (SEQ ID NO:10), VLAALP (SEQ ID NO:11), VLAALP (SEQ ID NO:11), VLPALA (SEQ ID NO:12), VLPALPQ (SEQ ID NO:13), VLAALPQ (SEQ ID NO:14), VLPALPA (SEQ ID NO:15), GVLPALP (SEQ ID NO:16), LQGVLPALPQVVC (SEQ ID NO:17), LPGCPRGVN-PVVS (SEQ ID NO:18), LPGC (SEQ ID NO:19), MTRV (SEQ ID NO:20), MTR, VVC, or functional analogues thereof, but other gene-regulatory peptides can also be selected. As described above, under certain circumstances it is preferred that the pharmaceutical composition is hypertonic. It may also be useful to add to the perfusion fluid an anticoagulant, such as heparin, or in conditions where disseminated intravascular coagulation (DIC) of the transplant is expected (such as with cadaveric donors) to add (recombinant) Activated Protein C to a perfusion fluid as herein provided. Where the Activated Protein C resolves the diffuse coagulation leading to ischemia, the NFκB-regulating peptide in the perfusion fluid helps reducing reperfusion damage. In most circumstances, the treatment with the preservation or perfusion fluid comprises providing the transplant with the signaling molecule after the transplant has been taken out of the donor. It is in particular useful to further treat the recipient with one of the above mentioned classically known pharmaceutical compositions for further reducing the risk of transplant rejection, especially in those cases wherein the HLA-type of the transplant mismatches with the HLA-type of the recipient.

The invention also provides a transplant preservation fluid or a transplant perfusion fluid comprising as a signaling molecule a peptide or functional analogue capable of modulating translocation and/or activity of a gene transcription factor.

In a specific embodiment, such a fluid also comprises (recombinant) Activated Protein C, especially when the gene transcription factor comprises an NFκB/Rel protein, or the AP-1 protein. The peptides added to such a fluid, such as LQG, AQG, LQGV (SEQ ID NO:1), AQGV (SEQ ID NO:2), LQGA (SEQ ID NO:3), VLPALP (SEQ ID NO:4), ALPALP (SEQ ID NO:5), VAPALP (SEQ ID NO:6), ALPALPQ (SEQ ID NO:7), VLPAAPQ (SEQ ID NO:8), VLPALAQ (SEQ ID NO:9), LAGV (SEQ ID NO:10), VLAALP (SEQ ID NO:11), VLPALA (SEQ ID NO:12), VLPALPQ (SEQ ID NO:13), VLAALPQ (SEQ ID NO:14), VLPALPA (SEQ ID NO:15), GVLPALP (SEQ ID NO:16), VVCNYRDVRFE-SIRLPGCPRGVNPVVSYAVALSCQCAL (SEQ ID NO:24), RPRCRPINATLAVEKEGCPVCITVNTTI-CAGYCPT (SEQ ID NO:25), SKAPPPSLPSPSRLPGPS (SEQ ID NO:26), LQGVLPALPQVVC (SEQ ID NO:17), SIRLPGCPRGVNPVVS (SEQ ID NO:27), LPGCPRGVN-PVVS (SEQ ID NO: 18), LPGC (SEQ ID NO:19), MTRV (SEQ ID NO:20), MTR, and VVC and others are, for example, prepared by solid-phase synthesis detailed description.

In response to a variety of pathophysiological and developmental signals, the NFκB/Rel family of transcription factors are activated and form different types of hetero- and homodimers among themselves to regulate the expression of target genes containing κB-specific binding sites. NFκB transcription factors are hetero- or homodimers of a family of related proteins characterized by the Rel homology domain. They form two subfamilies, those containing activation domains (p65-RELA, RELB, and c-REL) and those lacking activation domains (p50, p52). The prototypical NFκB is a heterodimer of p65 (RELA) and p50 (NFκB1). Among the activated NFκB dimers, p50-p65 heterodimers are known to be involved in enhancing the transcription of target genes and p50-p50 homodimers in transcriptional repression. However, p65-p65 homodimers are known for both transcriptional activation and repressive activity against target genes. κB DNA-binding sites with varied affinities to different NFB dimers have been discovered in the promoters of several eukaryotic genes and the balance between activated NFκB homo- and heterodimers ultimately determines the nature and level of gene expression within the cell. The term "NFκB-regulating peptide" as used herein refers to a peptide or a modification or derivative thereof capable of modulating the activation of members of the NFκB/Rel family of transcription factors. Activation of NFκB can gene-regulatory to enhanced transcription of target genes. Also, it can gene-regulatory to transcriptional repression of target genes. NFκB activation can be regulated at multiple levels. For example, the dynamic shuttling of the inactive NFκB dimers between the cytoplasm and nucleus by IκB proteins and its termination by phosphorylation and proteasomal degradation, direct phosphorylation, acetylation of NFκB factors, and dynamic reorganization of NFκB subunits among the activated NFκB dimers have all been identified as key regulatory steps in NFκB activation and, consequently, in NFκB-mediated transcription processes. Thus, an NFκB-regulating peptide is capable of modulating the transcription of genes that are under the control of NFκB/Rel family of transcription factors. Modulating comprises the up-regulation or the down-regulation of transcription. In a preferred embodiment, a peptide according to the invention, or a functional derivative or analogue thereof is used for the production of a pharmaceutical composition. Examples of useful NFκB down-regulating peptides to be included in such a pharmaceutical composition are VLPALPQVVC (SEQ ID NO:21), LQGVLPALPQ (SEQ ID NO:22), LQG, LQGV (SEQ ID NO: 1), GVLPALPQ (SEQ ID NO:23), VLPALP (SEQ ID NO:4), VVC, MTR and circular LQGVLPALPQVVC (SEQ ID NO:17). More gene-regulating peptides and functional analogues can be found in a (bio)assay, such as an NFκB translocation assay as pro vided herein. Most prominent among NFκB down-regulating peptides are VLPALPQVVC (SEQ ID NO:21), LQGVL-PALPQ (SEQ ID NO:22), LQG, LQGV (SEQ ID NO:1), and VLPALP (SEQ ID NO:4). These are also capable of reducing production of NO by a cell. It is herein also provided to use a composition that comprises at least two oligopeptides or functional analogues thereof, each capable of down-regulation NFκB, and thereby reducing production of NO and/or TNF-α by a cell, in particular wherein the at least two oligopeptides are selected from the group LQGV (SEQ ID NO:1), AQGV (SEQ ID NO:2), and VLPALP (SEQ ID NO:4). Useful NFκB up-regulating peptides are VLPALPQ (SEQ ID NO:13), GVLPALP (SEQ ID NO:16) and MTRV (SEQ ID NO:20). As indicated, more gene-regulatory peptides may be founds with an appropriate (bio)assay. A gene-regulatory peptide as used herein is preferably short. Preferably, such a peptide is 3 to 15 amino acids long, and capable of modulating the expression of a gene, such as a cytokine, in a cell. In a preferred embodiment, a peptide is a signaling molecule that is capable of traversing the plasma membrane of a cell or, in other words, a peptide that is membrane-permeable. More preferably, wherein the lead peptide is 3 to 9 amino acids long, most preferred wherein the lead peptide is 4 to 6 amino acids long.

Functional derivative or analogue herein relates to the signaling molecular effect or activity as, for example, can be measured by measuring nuclear translocation of a relevant transcription factor, such as NFκB in an NFκB assay, or AP-1 in an AP-1 assay, or by another method as provided herein.

Fragments can be somewhat (i.e., one or two amino acids) smaller or larger on one or both sides, while still providing functional activity. Such a bioassay comprises an assay for obtaining information about the capacity or tendency of a peptide, or a modification thereof, to regulate expression of a gene. A scan with, for example, a 15-mer, or a 12-mer, or a 9-mer, or a 8-mer, or a 7-mer, or a 6-mer, or a 5-mer, or a 4-mer or a 3-mer peptides can yield valuable information on the linear stretch of amino acids that form an interaction site and allows identification of gene-regulatory peptides that have the capacity or tendency to regulate gene expression. Gene-regulatory peptides can be modified to modulate their capacity or tendency to regulate gene expression, which can be easily assayed in an in vitro bioassay such as a reporter assay. For example, some amino acid at some position can be replaced with another amino acid of similar or different properties. Alanine (Ala)-replacement scanning, involving a systematic replacement of each amino acid by an Ala residue, is a suitable approach to modify the amino acid composition of a gene-regulatory peptide when in a search for a signaling molecule capable of modulating gene expression. Of course, such replacement scanning or mapping can be undertaken with amino acids other than Ala as well, for example, with D-amino acids. In one embodiment, a peptide derived from a naturally occurring polypeptide is identified as being capable of modulating gene expression of a gene in a cell. Subsequently, various synthetic Ala-mutants of this gene-regulatory peptide are produced. These Ala-mutants are screened for their enhanced or improved capacity to regulate expression of a gene compared to gene-regulatory polypeptide.

Furthermore, a gene-regulatory peptide, or a modification or analogue thereof, can be chemically synthesized using D- and/or L-stereoisomers. For example, a gene-regulatory peptide that is a retro-inverso of an oligopeptide of natural origin is produced. The concept of polypeptide retro-inversion (assemblage of a natural L-amino acid-containing parent sequence in reverse order using D-amino acids) has been applied successfully to synthetic peptides. Retro-inverso modification of peptide bonds has evolved into a widely used peptidomimetic approach for the design of novel bioactive molecules which has been applied to many families of biologically active peptide. The sequence, amino acid composition and length of a peptide will influence whether correct assembly and purification are feasible. These factors also determine the solubility of the final product. The purity of a crude peptide typically decreases as the length increases. The yield of peptide for sequences less than 15 residues is usually satisfactory, and such peptides can typically be made without difficulty. The overall amino acid composition of a peptide is an important design variable. A peptide's solubility is strongly influenced by composition. Peptides with a high content of hydrophobic residues, such as Leu, Val, Ile, Met, Phe and Trp, will either have limited solubility in aqueous solution or be completely insoluble. Under these conditions, it can be difficult to use the peptide in experiments, and it may be difficult to purify the peptide if necessary. To achieve a good solubility, it is advisable to keep the hydrophobic amino acid content below 50% and to make sure that there is at least one charged residue for every five amino acids. At physiological pH Asp, Glu, Lys, and Arg all have charged side chains. A single conservative replacement, such as replacing Ala with Gly, or adding a set of polar residues to the N- or C-terminus, may also improve solubility. Peptides containing multiple Cys, Met, or Trp residues can also be difficult to obtain in high purity partly because these residues are susceptible to oxidation and/or side reactions. If possible, one should choose sequences to minimize these residues. Alternatively, conservative replacements can be made for some residues. For instance, Norleucine can be used as a replacement for Met, and Ser is sometimes used as a less reactive replacement for Cys. If a number of sequential or overlapping peptides from a protein sequence are to be made, making a change in the starting point of each peptide may create a better balance between hydrophilic and hydrophobic residues. A change in the number of Cys, Met, and Trp residues contained in individual peptides may produce a similar effect. In another embodiment of the invention, a gene-regulatory peptide capable of modulating gene expression is a chemically modified peptide. A peptide modification includes phosphorylation (e.g., on a Tyr, Ser or Thr residue), N-terminal acetylation, C-terminal amidation, C-terminal hydrazide, C-terminal methyl ester, fatty acid attachment, sulfonation (tyrosine), N-terminal dansylation, N-terminal succinylation, tripalmitoyl-S-Glyceryl Cysteine (PAM3 Cys-OH) as well as farnesylation of a Cys residue. Systematic chemical modification of a gene-regulatory peptide can, for example, be performed in the process of gene-regulatory peptide optimization.

Synthetic peptides can be obtained using various procedures known in the art. These include solid phase peptide synthesis (SPPS) and solution phase organic synthesis (SPOS) technologies. SPPS is a quick and easy approach to synthesize peptides and small proteins. The C-terminal amino acid is typically attached to a cross-linked polystyrene resin via an acid labile bond with a linker molecule. This resin is insoluble in the solvents used for synthesis, making it relatively simple and fast to wash away excess reagents and by-products.

The peptides as mentioned in this document such as LQG, AQG, LQGV (SEQ ID NO:1), AQGV (SEQ ID NO:2), LQGA (SEQ ID NO:3), VLPALP (SEQ ID NO:4), ALPALP (SEQ ID NO:5), VAPALP (SEQ ID NO:6), ALPALPQ (SEQ ID NO:7), VLPAAPQ (SEQ ID NO:8), VLPALAQ (SEQ ID NO:9), LAGV (SEQ ID NO:10), VLAALP (SEQ ID NO:11), VLPALA (SEQ ID NO:12), VLPALPQ (SEQ ID NO:13), VLAALPQ (SEQ ID NO:14), VLPALPA (SEQ ID NO:15), GVLPALP (SEQ ID NO:16), VVCNYRDVRFE-SIRLPGCPRGVNPVVSYAVALSCQCAL (SEQ ID NO:24), RPRCRPINATLAVEKEGCPVCITVNTTI-CAGYCPT (SEQ ID NO:25), SKAPPPSLPSPSRLPGPS (SEQ ID NO:26), LQGVLPALPQVVC (SEQ ID NO:17), SIRLPGCPRGVNPVVS (SEQ ID NO:27), LPGCPRGVN-PVVS (SEQ ID NO:18), LPGC (SEQ ID NO:19), MTRV (SEQ ID NO:20), MTR, and VVC were prepared by solid-phase synthesis using the fluorenylmethoxycarbonyl (Fmoc)/tert-butyl-based methodology with 2-chlorotrityl chloride resin as the solid support. The side-chain of glutamine was protected with a trityl function. The peptides were synthesized manually. Each coupling consisted of the following steps: (i) removal of the α-amino Fmoc-protection by piperidine in dimethylformamide (DMF), (ii) coupling of the Fmoc amino acid (3 eq) with diisopropylcarbodiimide (DIC)/1-hydroxybenzotriazole (HOBt) in DMF/N-methylformamide (NMP), and (iii) capping of the remaining amino functions with acetic anhydride/diisopropylethylamine (DIEA) in DMF/NMP. Upon completion of the synthesis, the peptide resin was treated with a mixture of trifluoroacetic acid (TFA)/ $H_2O$/triisopropylsilane (TIS) 95:2.5:2.5. After 30 minutes TIS was added until decolorization. The solution was evaporated in vacuo and the peptide precipitated with diethylether. The crude peptides were dissolved in water (50 to 100 mg/ml) and purified by reverse-phase high-performance liquid chromatography (RP-HPLC). HPLC conditions were: column: Vydac TP21810C18 (10×250 mm); elution system: gradient system of 0.1% TFA in water v/v (A) and 0.1% TFA in acetonitrile (ACN) v/v (B); flow rate 6 ml/minute; absorbance was detected from 190 to 370 nm. There were different gradient systems used. For example, for peptides LQG and LQGV (SEQ ID NO:1): ten minutes 100% A followed by linear gradient 0 to 10% B in 50 minutes. For example, for peptides VLPALP (SEQ ID NO:4) and VLPALPQ (SEQ ID NO:13): five minutes 5% B followed by linear gradient 1% B/minute. The collected fractions were concentrated to about 5 ml by rotation film evaporation under reduced pressure at 40° C. The remaining TFA was exchanged against acetate by eluting two times over a column with anion exchange resin (Merck II) in acetate form. The elute was concentrated and lyophilized in 28 hours. Peptides later were prepared for use by dissolving them in PBS.

RAW 264.7 macrophages, obtained from American Type Culture Collection (Manassas, Va.), were cultured at 37° C. in 5% $CO_2$ using DMEM containing 10% FBS and antibiotics (100 U/ml of penicillin, and 100 μg/ml streptomycin). Cells ($1\times10^6$/ml) were incubated with peptide (10 μg/ml) in a volume of 2 ml. After eight hours of cultures cells were washed and prepared for nuclear extracts.

Nuclear extracts and EMSA were prepared according to Schreiber et al. Methods (Schrieber et al. 1989, *Nucleic Acids Research* 17). Briefly, nuclear extracts from peptide-stimulated or nonstimulated macrophages were prepared by cell lysis followed by nuclear lysis. Cells were then suspended in 400 μl of buffer (10 mM HEPES (pH 7.9), 10 mM KCl, 0.1 mM KCL, 0.1 mM EDTA, 0.1 mM EGTA, 1 mM DTT, 0.5 mM PMSF and protease inhibitors), vigorously vortexed for 15 seconds, left standing at 4° C. for 15 minutes, and centrifuged at 15,000 rpm for two minutes. The pelleted nuclei were resuspended in buffer (20 mM HEPES (pH 7.9), 10% glycerol, 400 mM NaCl, 1 mM EDTA, 1 mM EGTA, 1 mM DTT, 0.5 mM PMSF and protease inhibitors) for 30 minutes on ice, then the lysates were centrifuged at 15,000 rpm for two minutes. The supernatants containing the solubilized nuclear proteins were stored at −70° C. until used for the Electrophoretic Mobility Shift Assays (EMSA).

Electrophoretic mobility shift assays were performed by incubating nuclear extracts prepared from control (RAW 264.7) and peptide-treated RAW 264.7 cells with a 32P-labeled double-stranded probe (5' AGCTCAGAGGGG-GACTTTCCGAGAG 3' (SEQ ID NO:28)) synthesized to represent the NFκB-binding sequence. Shortly, the probe was end-labeled with T4 polynucleotide kinase according to the manufacturer's instructions (Promega, Madison, Wis.). The annealed probe was incubated with nuclear extract as follows: in EMSA, binding reaction mixtures (20 μl) contained 0.25 μg of poly(dI-dC) (Amersham Pharmacia Biotech) and 20,000 rpm of 32P-labeled DNA probe in binding buffer consisting of 5 mM EDTA, 20% Ficoll, 5 mM DTT, 300 mM KCl and 50 mM HEPES. The binding reaction was started by the addition of cell extracts (10 μg) and was continued for 30 minutes at room temperature. The DNA-protein complex was resolved from free oligonucleotide by electrophoresis in a 6% polyacrylamide gel. The gels were dried and exposed to x-ray films.

The transcription factor NFκB participates in the transcriptional regulation of a variety of genes. Nuclear protein extracts were prepared from LPS and peptide-treated RAW264.7 cells or from LPS-treated RAW264.7 cells. In order to determine whether the peptide modulates the translocation of NFκB into the nucleus, on these extracts EMSA was performed. Here we see that indeed peptides are able to modulate the translocation of NFκB since the amount of labeled oligonucleotide for NFκB is reduced. In this experiment peptides that show the modulation of translocation of NFκB are: VLPALPQVVC (SEQ ID NO:21), LQGVL-PALPQ (SEQ ID NO:22), LQG, LQGV (SEQ ID NO:1), GVLPALPQ (SEQ ID NO:23), VLPALP (SEQ ID NO:4), VLPALPQ (SEQ ID NO:13), GVLPALP (SEQ ID NO:16), VVC, MTRV (SEQ ID NO:20), MTR.

RAW 264.7 mouse macrophages were cultured in DMEM, containing 10% or 2% FBS, penicillin, streptomycin and glutamine, at 37° C., 5% $CO_2$. Cells were seeded in a 12-wells plate ($3\times10^6$ cells/ml) in a total volume of 1 ml for two hours and then stimulated with LPS (*E. coli* 026:B6; Difco Laboratories, Detroit, Mich., USA) and/or gene-regulatory peptide (1 microgr/ml). After 30 minutes of incubation, plates were centrifuged and cells were collected for nuclear extracts. Nuclear extracts and EMSA were prepared according to Schreiber et al. Cells were collected in a tube and centrifuged for five minutes at 2000 rpm (rounds per minute) at 4° C. (Universal 30 RF, Hettich Zentrifuges). The pellet was washed with ice-cold Tris buffered saline (TBS pH 7.4) and resuspended in 400 μl of a hypotonic buffer A (10 mM HEPES pH 7.9, 10 mM KCl, 0.1 mM EDTA, 0.1 mM EGTA, 1 mM DTT, 0.5 mM PMSF and protease inhibitor cocktail (Complete™ Mini, Roche) and left on ice for 15 minutes. Twenty-five microliters 10% NP-40 was added and the sample was centrifuged (two minutes, 4000 rpm, 4° C.). The supernatant (cytoplasmic fraction) was collected and stored at −70° C. The pellet, which contains the nuclei, was washed with 50 μl buffer A and resuspended in 50 μl buffer C (20 mM HEPES pH 7.9, 400 mM NaCl, 1 mM EDTA, 1 mM EGTA, 1 mM DTT, 0.5 mM PMSF and protease inhibitor cocktail and 10% glycerol). The samples were left to shake at 4° C. for at least 60 minutes. Finally the samples were centrifuged and the supernatant (nucleic fraction) was stored at −70° C.

Bradford reagent (Sigma) was used to determine the final protein concentration in the extracts. For electrophoretic mobility shift assays an oligonucleotide representing NFκB-binding sequence (5'-AGC TCA GAG GGG GAC TTT CCG AGA G-3' (SEQ ID NO:28)) was synthesized. Hundred pico mol sense and antisense oligo were annealed and labeled with γ-$^{32}$P-dATP using T4 polynucleotide kinase according to the manufacturer's instructions (Promega, Madison, Wis.). Nuclear extract (5 to 7.5 μg) was incubated for 30 minutes with 75000 cpm probe in binding reaction mixture (20 microliters) containing 0.5 μg poly dI-dC (Amersham Pharmacia Biotech) and binding buffer BSB (25 mM $MgCl_2$, 5 mM $CaCl_2$, 5 mM DTT and 20% Ficoll) at room temperature. The DNA-protein complex was resolved from free oligonucleotide by electrophoresis in a 4 to 6% polyacrylamide gel (150 V, two to four hours). The gel was then dried and exposed to x-ray film. The transcription factor NFκB participates in the transcriptional regulation of a variety of genes. Nuclear protein extracts were prepared from either LPS (1 mg/ml), peptide (1 mg/ml) or LPS in combination with peptide-treated and untreated RAW264.7 cells. In order to determine whether the peptides modulate the translocation of NFκB into the nucleus, on these extracts EMSA was performed. Peptides are able to modulate the basal as well as LPS-induced levels of NFκB. In this experiment peptides that show the inhibition of LPS-induced translocation of NFκB are: VLPALPQVVC (SEQ ID NO:21), LQGVLPALPQ (SEQ ID NO:22), LQG, LQGV (SEQ ID NO:1), GVLPALPQ (SEQ ID NO:23), VLPALP (SEQ ID NO:4), VVC, MTR and circular LQGV-LPALPQVVC (SEQ ID NO: 17). Peptides that in this experiment promote LPS-induced translocation of NFκB are: VLPALPQ (SEQ ID NO:13), GVLPALP (SEQ ID NO:16) and MTRV (SEQ ID NO:20). Basal levels of NFκB in the nucleus was decreased by VLPALPQVVC (SEQ ID NO:21), LQGVLPALPQ (SEQ ID NO:22), LQG and LQGV (SEQ ID NO:1) while basal levels of NFκB in the nucleus was increased by GVLPALPQ (SEQ ID NO:23), VLPALPQ (SEQ ID NO:13), GVLPALP (SEQ ID NO:16), VVC, MTRV (SEQ ID NO:20), MTR and LQGVLPALPQVVC (SEQ ID NO:21). In other experiments, QVVC also showed the modulation of translocation of NFκB into nucleus (data not shown).

Further Modes of Identification of Gene-Regulatory Peptides by NFκB Analysis

Cells: Cells will be cultured in appropriate culture medium at 37° C., 5% $CO_2$. Cells will be seeded in a 12-wells plate (usually $1 \times 10^6$ cells/ml) in a total volume of 1 ml for two hours and then stimulated with regulatory peptide in the presence or absence of additional stimuli such as LPS. After 30 minutes of incubation plates will be centrifuged and cells are collected for cytosolic or nuclear extracts.

Nuclear Extracts: Nuclear extracts and EMSA could be prepared according to Schreiber et al., Method (Schriber et al. 1989, *Nucleic Acids Research* 17). Cells are collected in a tube and centrifuged for five minutes at 2000 rpm (rounds per minute) at 4° C. (Universal 30 RF, Hettich Zentrifuges). The pellet is washed with ice-cold Tris buffered saline (TBS pH 7.4) and resuspended in 400 μl of a hypotonic buffer A (10 mM HEPES pH 7.9, 10 mM KCl, 0.1 mM EDTA, 0.1 mM EGTA, 1 mM DTT, 0.5 mM PMSF and protease inhibitor cocktail (Complete™ Mini, Roche) and left on ice for 15 minutes. Twenty-five microliters 10% NP-40 is added and the sample is centrifuged (two minutes, 4000 rpm, 4° C.). The supernatant (cytoplasmic fraction) was collected and stored at −70° C. for analysis. The pellet, which contains the nuclei, is washed with 50 μl buffer A and resuspended in 50 μt buffer C (20 mM HEPES pH 7.9, 400 mM NaCl, 1 mM EDTA, 1 mM EGTA, 1 mM DTT, 0.5 mM PMSF and protease inhibitor cocktail and 10% glycerol). The samples are left to shake at 4° C. for at least 60 minutes. Finally the samples are centrifuged and the supernatant (nucleic fraction) is stored at −70° C. for analysis.

Bradford reagent (Sigma) could be used to determine the final protein concentration in the extracts.

EMSA: For Electrophoretic mobility shift assays an oligonucleotide representing NFκB-binding sequence such as (5'-AGC TCA GAG GGG GAC TTT CCG AGA G-3' (SEQ ID NO:28)) are synthesized. Hundred pico mol sense and antisense oligo are annealed and labeled with $\gamma$-$^{32}$P-dATP using T4 polynucleotide kinase according to the manufacturer's instructions (Promega, Madison, Wis.). Cytosolic extract or nuclear extract (5-7.5 μg) from cells treated with regulatory peptide or from untreated cells is incubated for 30 minutes with 75,000 cpm probe in binding reaction mixture (20 μl) containing 0.5 μg poly dI-dC (Amersham Pharmacia Biotech) and binding buffer BSB (25 mM $MgCl_2$, 5 mM $CaCl_2$, 5 mM DTT and 20% Ficoll) at room temperature. Or cytosolic and nuclear extract from untreated cells or from cells treated with stimuli could also be incubated with probe in binding reaction mixture and binding buffer. The DNA-protein complexes are resolved from free oligonucleotide by electrophoresis in a 4 to 6% polyacrylamide gel (150 V, two to four hours). The gel is then dried and exposed to x-ray film. Peptides can be biotinylated and incubated with cells. Cells are then washed with phosphate-buffered saline, harvested in the absence or presence of certain stimulus (LPS, PHA, TPA, anti-CD3, VEGF, TSST-1, VIP or know drugs etc.). After culturing cells are lysed and cells lysates (whole lysate, cytosolic fraction or nuclear fraction) containing 200 micrograms of protein are incubated with 50 microliters Neutr-Avidin-plus beads for one hour at 4° C. with constant shaking. Beads are washed five times with lysis buffer by centrifugation at 6000 rpm for one minute. Proteins are eluted by incubating the beads in 0.05 N NaoH for one minute at room temperature to hydrolyze the protein-peptide linkage and analyzed by SDS-polyacrylamide gel electrophoresis followed by immunoprecipitated with agarose-conjugated anti-NFκB subunits antibody or immunoprecipitated with antibody against to be studied target. After hydrolyzing the protein-peptide linkage, the sample could be analyzed on HPLS and mass-spectrometry. Purified NFκB subunits or cell lysate interaction with biotinylated regulatory peptide can be analyzed on biosensor technology. Peptides can be labeled with FITC and incubated with cells in the absence or presence of different stimulus. After culturing, cells can be analyzed with fluorescent microscopy, confocal microscopy, flow cytometry (cell membrane staining and/or intracellular staining) or cells lysates are made and analyzed on HPLC and mass-spectrometry. NFκB-transfected (reporter gene assay) cells and gene array technology can be used to determine the regulatory effects of peptides.

HPLC and mass-spectrometry analysis: Purified NFκB subunit or cytosolic/nuclear extract is incubated in the absence or presence of (regulatory) peptide is diluted (2:1) with 8 N guanidinium chloride and 0.1% trifluoroacetic acid, injected into a reverse-phase HPLC column (Vydac C18) equilibrated with solvent A (0.1% trifluoroacetic acid), and eluted with a gradient of 0 to 100% eluant B (90% acetonitrile in solvent A). Factions containing NFκB subunit are pooled and concentrated. Fractions are then dissolved in appropriate volume and could be analyzed on mass-spectrometry.

EXAMPLE

The invention in particular relates to the, preferably oral, treatment of neurological disorders or so called neuroimmune disorders such as schizophrenia, manic depression and other bipolar disorders, post-partum psychosis, autism, chronic fatigue syndrome (CFS), fibromyalgia, Alzheimers, mood disorders and certain forms of stress. Although there are major differences in etiology and mechanisms of pathogenesis of each of these syndromes and or diseases, there are in fact common inflammatory and immunomodulatory pathways that are shared within the pathogenesis of neurological disorders.

Evidence of immune abnormalities in patients suffering from psychological disease clearly shows the implication of the immune system in pathogenesis. Neuroimmune disorders have become recognized as common pathogenetic factors in the development of psycho- or neuropathologies. The neurochemical and immunologic findings indicate multiple pathways of the pathogenesis; herein, we discuss the role of inflammatory disease in neurological disorders. For example, chronic fatigue syndrome is a condition that affects women in disproportionate numbers, and that is often exacerbated in the premenstrual period and following physical exertion. The signs and symptoms, which include fatigue, myalgia, and low-grade fever, are similar to those experienced by patients infused with cytokines such as interleukin-1. In general, during the development of a neuroimmune disorder, the TNF-α family and other pro-inflammatory cytokines are highly elevated in cerebrospinal fluid (CSF), demonstrative of foci of inflammation in the brain leading to an array of destructive and degenerative responses directed at diverse areas in the CNS. Major mood disorders are leading causes of disability from early adolescence onward and leading sources of disease burden, surpassing cardiovascular diseases, dementia, lung cancer and diabetes. As said, there is a major role for inflammatory cytokines and immune cells in the pathophysiology of mood disorders, it was recently also found that T-cells and monocytes function at a higher, pro-inflammatory level in patients with bipolar disorder. Successful therapy of these destructive and degenerative disorders that affect the adult human central nervous system (CNS) will require the ability both to reduce the rate and extent of tissue injury, and to restore or replace destroyed tissue. Neuroimaging studies have shown that functional organization occurs spontaneously in the adult human brain in response to tissue insults. The extent of this compensatory mechanism may be limited, necessitating development of active methods of intervention. Replacement of a single neurotransmitter, neurohormone or trophic factor may suffice if the injury is limited or effected as a suppression or altered pathway within the CNS through proinflammatory regulators. The hippocampus is a source for mitotically active neuronal progenitor cells which can hypothetically replace neurons and myelinating cells. It is the control of these cells and the health and activity of other cells which offers new insight and hope of treating heretofore chronic CNS disease. It is areas such as cells in the adult human dentate gyrus which may be part of the key to controlling immunomodulation and growth support of the brain and its diverse functions which span from memory and cognition to its endocrine and immunologic activities. As with all complex traits, a neurological disorder results from an interplay between as yet unidentified environmental factors and susceptibility genes. Together, these factors trigger a cascade of events, involving engagement of the immune system, acute inflammatory injury of the central nervous system, notably axons and glia, recovery of function and structural repair, post-inflammatory gliosis, and neurodegeneration. The sequential involvement of these processes underlies the clinical course characterized by episodes with recovery interchanged with episodes leaving persistent deficits, episodes which we generally call psychological disorders.

For a more detailed example, although there are several forms of autism (which often present themselves already at birth) which may have clear genetic etiologies, the most common forms however occur long after normal births and are associated with proinflammatory cytokine dysregulation. According to recent epidemiological surveys, autistic spectrum disorders have become recognized as common childhood psychopathologies. These life-lasting conditions demonstrate a strong genetic determinant consistent with a polygenic mode of inheritance for which several autism susceptibility regions have been identified. Parallel evidence of immune abnormalities in autistic patients argues for an implication of the immune system in pathogenesis. This introduction summarizes advances in the molecular genetics of autism, as well as recently emerging concerns addressing the disease incidence and triggering factors. The neurochemical and immunologic findings are analyzed in the context of a neuroimmune hypothesis for specific neurological disorders. For example, pregnancy and the post partum period are important modulators of the immune system and the immune suppression in pregnancy is followed by an immune activation in the puerperium. In another example, autism is influenced by specific food allergies or even the early use of vaccines which may cause changes in the regulation of innate or acquired immunity and set up neuroendocrine dysfunction. Also, neurological disorders are often associated with autoimmune disorders in the patients' relatives. A. M. Comi et al. (*J. Child Neurol.* Jun. 14, 1999; (6):388-94) evaluated the frequency of autoimmune disorders, as well as various prenatal and postnatal events in autism, and surveyed the families of 61 autistic patients and 46 healthy controls using questionnaires. The mean number of autoimmune disorders was greater in families with autism; 46% had two or more members with autoimmune disorders. As the number of family members with autoimmune disorders increased from one to three, the risk of autism was greater, with an odds ratio that increased from 1.9 to 5.5, respectively. In mothers and first-degree relatives of autistic children, there were more autoimmune disorders (16% and 21%) as compared to controls (2% and 4%), with odds ratios of 8.8 and 6.0, respectively. The most common autoimmune disorders in both groups were type 1 diabetes, adult rheumatoid arthritis, hypothyroidism, and systemic lupus erythematosus. Forty-six percent of the autism group reported having relatives with rheumatoid diseases, as compared to 26% of the controls. Prenatal maternal urinary tract, upper respiratory, and vaginal infections; asphyxia; prematurity, and seizures were more common in the autistic group, although the differences were not significant. Thirty-nine percent of the controls, but only 11% of the autistic, group, reported allergies. The increased number of autoimmune disorders shows that in autism, immune dysfunction interacts with various environmental factors to play a role in autism pathogenesis. According to S. B. Edelson and D. S. Cantor (*Toxicol. Ind Health* Jul.-Aug. 14, 1998 (4):553-63) the advances in medical technology during the last four decades have provided evidence for an underlying neurological basis for autism. The etiology for the variations of neurofunctional anomalies found in the neurological disorder spectrum behaviors appears inconclusive as of this date but growing evidence supports the proposal that chronic exposure to toxic agents, i.e., xenobiotic agents, resulting in a inflammatory reaction directed towards a developing central nervous system may be the best model for defining the physiological and behavioral data found in these populations. Also, an examination of 18 autistic children in blood analyses that were available showed that 16 of these children showed evidence of levels of toxic chemicals exceeding adult maximum tolerance. In the two cases where toxic chemical levels were not found, there was abnormal D-glucaric acid findings suggesting abnormal xenobiotic influences on liver detoxification processes. A proposed mechanism for the interaction of xenobiotic toxins with immune system dysfunction and continuous and/or progressive endogenous toxicity is presented as it relates to the development of behaviors found in the autistic spectrum. H. Jyonouchi et al. (*J. Neuroimmunol.* Nov. 1, 2001; 120(1-2):170-9) determined innate and adaptive immune responses in children with developmental regression and autism spectrum disorders (ASD, N=71), developmentally normal siblings (N=23), and controls (N=17), and found a clear relationship between proinflammatory and regulatory cytokine production associated with innate and adaptive immune responses in children with autism spectrum disorders and developmental regression. With lipopolysaccharide (LPS), a stimulant for innate immunity, peripheral blood mononuclear cells (PBMCs) from 59/71 (83.1%) ASD patients produced >2 SD above the control mean (CM) values of TNF-α, IL-1β, and/or IL-6 produced by control PBMCs. ASD PBMCs produced higher levels of proinflammatory/counter-regulatory cytokines without stimuli than controls. With stimulants of phytohemagglutinin (PHA), tetanus, IL-12p70, and IL-18, PBMCs from 47.9% to 60% of ASD patients produced >2 SD above the CM values of TNF-α depending on stimulants. These results indicate excessive innate immune responses as a result of NFκB-induced cytokine expression in a number of ASD children that is most evident in TNF-α production. Furthermore, according to S. Messahel et al. (*Neurosci. Lett.* Jan. 23, 1998; 241(1):17-20) the pterins, neopterin and biopterin, occur naturally in body fluids including urine. It is well established that increased neopterin levels are associated with activation of the cellular immune system and that reduced biopterins are essential for neurotransmitter synthesis. It has been also been suggested that some autistic children may be suffering from an autoimmune disorder. To investigate this further the above authors performed high performance liquid chromatography analyses of urinary pterins in a group of pre-school autistic children, their siblings and age-matched control children. Both urinary neopterin and biopterin were raised in the autistic children compared to controls and the siblings showed intermediate values.

As yet another example, the chronic fatigue syndrome (CFS) is a clinically defined condition characterized by severe disabling fatigue and a combination of symptoms that prominently features self-reported impairments in concentration and short-term memory, sleep disturbances, and musculoskeletal pain. Heretofore, the diagnosis of the chronic fatigue syndrome could only be made after other medical and psychiatric causes of chronic fatiguing illness were excluded. No pathognomonic signs or clear diagnostic tests for this condition have yet been validated. Thus far, no definitive treatment exists. Recent longitudinal studies suggest that some persons affected by the chronic fatigue syndrome improve with time but that most remain functionally impaired for several years. CFS is characterized by debilitating fatigue that is not attributable to known clinical conditions, that has lasted for >6 months, that has reduced the activity level of a previously healthy person by >50%, and that has been accompanied by flu-like symptoms (e.g., pharyngitis, adenopathy, low grade fever, myalgia, arthralgia, headache) and neuropsychological manifestations (e.g., difficulty concentrating, exercise intolerance, and sleep disturbances). CFS is frequently of sudden onset. There have been considerable advances in our understanding of the mediators of CFS, with several careful studies of immunologic function, activation, and cytokine dysregulation. An increasing number of independent groups have reported abnormalities of both T- and B-cell lymphocyte and NK cell function, with one group correlating levels of NK cell function to disease severity. It was suggested that the illness be named chronic immune activation syndrome given the abnormally elevated markers of T-cell activation measured on T-cells and cytotoxic T-cells.

Over the last decade, investigators have demonstrated that individuals with CFS have significantly increased proportions of activated CD8+ T-cells, decreased natural killer cell (NK) cytotoxic and lymphoproliferative activities, elevated serum levels of tumor necrosis factor (TNF)-$\alpha$ and $\beta$, and detectable TNF-$\beta$, interleukin (IL)-1$\beta$ and IL-6 mRNA in peripheral blood mononuclear cells (PBMC). CFS patients, as a group, also have significantly higher levels, as compared to controls, of soluble TNF receptor type I (sTNF-RI), sIL-6R and $\beta$2-microglobulin ($\beta$2-m), but not of IL-1 receptor antagonist (IL-1Ra). Correlative and population distribution studies that included lymphoid phenotypic distributions and function as well as soluble immune mediator expression levels revealed the existence of at least two mainly nonoverlapping categories among CFS patients with either: (1) dysregulated TNF-$\alpha$/$\beta$ expression in association with changes in the serum levels of IL-1$\alpha$, IL-4, sIL-2R, and IL-1Ra, PBMC-associated expression of IL-1$\beta$, IL-6, and TNF-$\beta$ mRNA, and T-cell activation; or (2) interrelated and dysregulated expression of sTNF-R1, sIL-6R, and $\beta$2-microglobulin and significantly decreased lymphoproliferative and NK cell cytotoxic activities. Furthermore, allostasis—the ability to achieve stability through change—is critical to survival, and many psychological disorders are manifestations of the fact that such stability is not present. Through allostasis, the autonomic nervous system, the hypothalamic-pituitary-adrenal (HPA) axis, and the cardiovascular, metabolic, and immune systems protect the body by responding to internal and external stress. The price of this accommodation to stress can be allostatic load, which is the wear and tear that results from chronic overactivity or underactivity of allostatic systems.

The core of the body's response to a challenge is twofold, turning on an allostatic response that initiates a complex adaptive pathway, and then shutting off this response when the threat is past. The most common allostatic responses involve the sympathetic nervous systems and the HPA axis. For these systems, activation releases catecholamines from nerves and the adrenal medulla and leads to the secretion of corticotropin from the pituitary. The corticotropin, in turn, mediates the release of cortisol from the adrenal cortex. Inactivation returns the systems to base-line levels of cortisol and catecholamine secretion, which normally happens when the danger is past. However, if the inactivation is inefficient, there is overexposure to stress hormones. Over weeks, months, or years, exposure to increased secretion of stress hormones results in a so-called allostatic load and its immunopathophysiologic consequences. It has been shown that allostatic load over a lifetime may cause the allostatic systems to wear out or become exhausted. Frailty in old age is generally seen as a consequence of a worn-out allostatic system. A vulnerable link in the regulation of the HPA axis and cognition is the hippocampal region. Wear and tear on this region of the brain leads to dysregulation of the HPA axis and cognitive impairment. Indeed, some, but not all, of the aging people have impairment of episodic, declarative, and spatial memory and hyperactivity of the HPA axis, all of which can be traced to inflammatory hippocampal damage. Recent data show that similar events occur at a younger age in humans with unexplained mood disorders. In one type of allostatic load inadequate responses by some allostatic systems trigger compensatory increases in others. When one system does not respond adequately to a stressful stimulus, the activity of other systems increases, because the underactive system is not providing the usual counter-regulation. For example, if cortisol secretion does not increase in response to stress, secretion of inflammatory cytokines (which are counter-regulated by cortisol) increases. The negative consequences of an enhanced inflammatory response are, for example, that the affected subjects are very susceptible to autoimmune and inflammatory disturbances, aggravated often by a genetically determined hyporesponsiveness of the HPA axis.

Also, the months following childbirth are a time when some women are susceptible to serious mood disorders. The illnesses can be resistant to conventional psychiatric treatment methods. Cases of postpartum depression or puerperal psychosis often occur in women with a past history of major depression or bipolar disorder. There has been considerable debate as to whether postpartum psychosis is a discrete diagnostic entity or whether it represents a rapidly evolving psychosis, that is a manifestation of an underlying bipolar (or manic-depressive) disorder. To date, existing psychiatric research supports the latter view.

The invention provides a method for the treatment of a subject believed to be suffering from a neurological disorder, with a specific aim of reducing the frequency, and limit the lasting effects of the psychological manifestations of neuroimmune disease, and in particular the treatment of the inflammatory component of neurological or mood disorders to relieve symptoms that arise from the release of additional pro-inflammatory cytokines, in particular during disease progression, to prevent disability arising from disease progression, and to promote CNS tissue repair. The invention provides a pharmaceutical composition, in particular for oral administration, for the treatment of a neurological disorder occurring in a subject, for example, in a primate, and a method for the treatment of the disease associated with additional pro-inflammatory cytokine release, for example, in a primate comprising subjecting the subject to a signaling molecule according to the invention, preferably to a mixture of such signaling molecules. The invention aims at countering the involvement of cell-mediated immunity in the etiology of neurological disease, and treating the inflammatory component of neurological disorders by targeting the central role of NFκB-induced cytokine expression. As a consequence of (likely CNS-based) NFκB expression, toxic inflammatory mediators are released, sustaining breakdown of the blood-brain barrier and leading to injury of axons and glia. Nitric oxide might act directly on normal or hypomyelinated axons, transiently blocking conduction and reversibly increasing deficits arising from already compromised pathways. As acute inflammation resolves, pathways are released from nitric oxide-induced physiological conduction block. Symptoms also improve as surviving functional pathways are reorganized at the cellular and systems level. Together, these mechanisms account for remission early in the disease. But tissue vulnerability is easily exposed. When compounded by high axonal firing frequency, nitric oxide causes structural (and hence irreversible) changes to axons. Cytokines and growth-promoting factors released by reactive astrocytes and microglia as part of the acute inflammatory process promote endogenous remyelination. But, over time, astrocyte reactivity seals the lesion and gliosis causes a physical barrier to further remyelination, reducing the capacity to accommodate cumulative deficits, and marking transition to the stage of persistent deficit. Since permanent disability can be caused by incomplete recovery from the inflammation, the invention provides a method for modulating a neurological disorder in a subject believed to be in need thereof comprising providing the subject with a signaling molecule comprising a short, gene-regulatory peptide or functional analogue thereof, wherein the signaling molecule is administered in an amount sufficient to modulate the exacerbating event. The signal molecule is preferably a short peptide, preferably at most 30 amino acids long, or a functional analogue or derivative thereof. In a much preferred embodiment, the peptide is an oligopeptide of from about 3 to about 15 amino acids long, preferably 4 to 12, more preferably 4 to 9, most preferably 4 to 6 amino acids long, or a functional analogue or derivative thereof. For oral treatment, it is preferably 3 to 6, even more preferably 3 to 5, most preferably 3 or 4 amino acids long. Most preferred for oral treatment is a peptide selected from the group of peptides LQG, QVV, PALP (SEQ ID NO:34), AQG, LAG, LQGV (SEQ ID NO:1), AQGV (SEQ ID NO:2), or LAGV (SEQ ID NO:10). Of course, such signaling molecule can be longer, for example, by extending it (N- and/or C-terminally), with more amino acids or other side groups, which can, for example, be (enzymatically) cleaved off when the molecule enters the place of final destination, however, by virtue of its small size of smaller than 15, preferably smaller than nine amino acids, even more preferably smaller then six amino acids, a peptide or functional analogue according to the invention thereof readily be taken up by the intestinal mucosae after oral administration and readily be crossing the blood brain barrier. Furthermore such a small peptide as provided herein is very stable and has a pharmaceutical half life greater than four hours. Herewith, the invention also provides a method of, preferably oral, treatment of mood disorders such as cases of postpartum depression or puerperal psychosis and a use of a signal molecule according to the invention for the preparation of a pharmaceutical composition for the treatment of cases of postpartum depression or puerperal psychosis, in particular by at least partly restoring or mimicking the anti-inflammatory activity of the gene-regulatory peptides LQGV (SEQ ID NO:1), AQGV (SEQ ID NO:2), and VLPALP (SEQ ID NO:4) and their functional analogues. In particular a method is provided wherein the signaling molecule modulates translocation and/or activity of a gene transcription factor. It is particularly useful when the gene transcription factor comprises an NFκB/Rel protein or an AP-1 protein. Many of the neurological disorders events as mentioned above involve increased expression of inflammatory cytokines due to activation of NFκB and AP-1, and in a preferred embodiment the invention provides a method wherein translocation and/or activity of the NFκB/Rel protein or AP-1 protein is inhibited. In this way, the destruction of brain tissues like the myelin lining of nerves or plaque formation which disrupts the brain which have been found to be significantly based on autoimmune or proinflammatory destruction caused by a dysregulated release of cytokines and chemokines is inhibited by an oral treatment according to the invention. In one embodiment, the peptide is selected from the group of synthetic peptides LQG, AQG, LQGV (SEQ ID NO:1), AQGV (SEQ ID NO:2), LQGA (SEQ ID NO:3), VLPALP (SEQ ID NO:4), ALPALP (SEQ ID NO:5), VAPALP (SEQ ID NO:6), ALPALPQ (SEQ ID NO:7), VLPAAPQ (SEQ ID NO:8), VLPALAQ (SEQ ID NO:9), LAGV (SEQ ID NO:10), VLAALP (SEQ ID NO:11), VLPALA (SEQ ID NO:12), VLPALPQ (SEQ ID NO:13), VLAALPQ (SEQ ID NO:14), VLPALPA (SEQ ID NO:15), GVLPALP (SEQ ID NO:16), LQGVLPALPQVVC (SEQ ID NO:17), LPGCPRGVNPVVS (SEQ ID NO:18), LPGC (SEQ ID NO:19), MTRV (SEQ ID NO:20), MTR, VVC, which is used for the preparation of a pharmaceutical composition. As said, additional expression of inflammatory cytokines is often due to activation of NFκB and AP-1. Inflammatory cytokines can be expressed by endothelium, perivascular cells and adherent or transmigrating leukocytes, all inducing numerous pro-inflammatory and procoagulant effects. Together these effects predispose to inflammation, thrombosis and hemorrhage. Of clinical and medical interest and value, the present invention provides the opportunity to selectively control NFκB-dependent gene expression in tissues and organs in a living subject, preferably in a primate, allowing up-regulating essentially anti-inflammatory responses such as IL-10, and down-regulating essentially pro-inflammatory responses such as mediated by TNF-α, nitric oxide (NO), IL-5, IL-6 and IL-1β.

The invention thus provides use of an NFκB-regulating peptide or derivative thereof for the production of a pharmaceutical composition for the treatment of neurological disorders, preferably in a primate, and provides a method of treatment of neurological disorders, notably in a primate. It is preferred when the treatment comprises administering to the subject a pharmaceutical composition comprising an NFκB down-regulating peptide or functional analogue thereof. Examples of useful NFκB down-regulating peptides are VLPALPQVVC (SEQ ID NO:21), LQGVLPALPQ (SEQ ID NO:22), LQG, LQGV (SEQ ID NO:1), GVLPALPQ (SEQ ID NO:23), VLPALP (SEQ ID NO:4), VVC, MTR and circular LQGVLPALPQVVC. More down-regulating peptides and functional analogues can be found using the methods as provided herein. Most prominent among NFκB down-regulating peptides are VLPALPQVVC (SEQ ID NO:21), LQGVLPALPQ (SEQ ID NO:22), LQG, LQGV (SEQ ID NO:1), and VLPALP (SEQ ID NO:4). These are also capable of reducing production of NO by a cell. It is herein also provided to use a composition that comprises at least two oligopeptides or functional analogues thereof, each capable of down-regulation NFκB, and thereby reducing production of NO and/or TNF-α by a cell, in particular wherein the at least two oligopeptides are selected from the group LQGV (SEQ ID NO:1), AQGV (SEQ ID NO:2), and VLPALP (SEQ ID NO:4), for the treatment of recurring disease seen with neurological disorders. In a preferred embodiment, a peptide according to the invention, or a functional derivative or analogue thereof is used for the production of a pharmaceutical composition for the oral treatment of neurological disorders. NFκB-regulating peptide can be given alone or concomitantly to other treatments, the peptide (or analogue) concentration preferably being from about 1 to about 1000 mg/l, but the peptide can also been given on its own, for example, in a bolus injection or oral preparation. In acute cases, doses of 1 to 5 mg/kg bodyweight, for example, every eight hours in a bolus injection or per infusionem until the patient stabilizes, are recommended, however, maintenance dosages afterwards are preferably administered orally. For example, in cases where large adverse response are expected or diagnosed, it is preferred to monitor cytokine profiles, such as TNF-α, IL-6 or IL-10 levels, in the plasma of the treated patient, and to stop treatment according to the invention when these levels are normal. In a preferred embodiment it is herein provided to provide the patient experiencing a severe and acute bipolar disorder with a bolus injection of NFκB down-regulating peptide such as AQGV (SEQ ID NO:2), LQGV (SEQ ID NO:1) or VLPALP (SEQ ID NO:4) at 2 mg/kg and continue the infusion with an NFκB-down-regulating peptide such as AQGV (SEQ ID NO:2), LQGV (SEQ ID NO:1) or VLPALP (SEQ ID NO:4) or a functional analogue thereof at a dose of 1 mg/kg bodyweight for every eight hours. Dosages may be increased or decreased, for example, depending on the outcome of monitoring the cytokine profile in the plasma or CSF of the patient. As said, disease progression is dramatically mediated by cytokines and chemokines. For example, the TNF-α family is then highly elevated in CSF. The down-regulation or T-cell regulation of these cytokines and chemokines can prevent T-cell and dendritic cells from reaching the CNS and then further down-regulate the proinflammatory response which produces pathology of the brain and spinal cord. This model of migration of cells to the CNS and then the release of proinflammatory cytokines and chemokines is seen in the following and can be treated by a peptide according to the invention through NFκB regulation, the development of T-regulator cells, and the intervention of expression early or pregenes such as C-jun or C-erg. For the pathologist, neurological disorders often present as a disorder of the central nervous system, manifesting as acute focal inflammatory demyelination and axonal loss with limited remyelination. Thus, the primary nature of inflammation is undisputed and is central for treatments that modulate the immune system. There are, however, several aspects that limit the therapeutic efficacy of strategies directed against the inflammatory component of the disease. Currently, immune suppression with corticosteroids is unable to specifically stop the inflammatory regimes. Also, the inflammatory forms of neurological disorder, such as described above with autism, which are now epidemic in United States and European studies responds well in part to the use of an NFκB-down-regulating peptides according to the invention.

It is herein also provided to use a composition that comprises at least two oligopeptides or functional analogues thereof, each capable of down-regulation NFκB, and thereby reducing production of NO and/or TNF-α by a cell, in particular wherein the at least two oligopeptides are selected from the group LQGV (SEQ ID NO:1), AQGV (SEQ ID NO:2), and VLPALP (SEQ ID NO:4). Useful NFκB up-regulating peptides are VLPALPQ (SEQ ID NO:13), GVL-PALP (SEQ ID NO:16) and MTRV (SEQ ID NO:20). As indicated, more gene-regulatory peptides may be found with an appropriate (bio)assay. A gene-regulatory peptide as used herein is preferably short. Preferably, such a peptide is 3 to 15 amino acids long, more preferably, wherein the lead peptide is 3 to 9 amino acids long, most preferred wherein the lead peptide is 4 to 6 amino acids long, and capable of modulating the expression of a gene, such as a cytokine, in a cell. In a preferred embodiment, a peptide is a signaling molecule that is capable of traversing the plasma membrane of a cell or, in other words, a peptide that is membrane-permeable.

EXAMPLE

This invention in particular relates to the, preferably oral, treatment of multiple sclerosis, and in particular to the, preferably oral, treatment of the inflammatory injury seen in the progressive stages in the disease such as seen with the recurrent upsurges of acute disease, classically known as relapses or exacerbations, herein identified as relapsing/remitting disease seen with multiple sclerosis (MS).

Multiple sclerosis (MS) is the prototype inflammatory autoimmune disorder of the central nervous system and, with a lifetime risk of one in 400, potentially the most common cause of neurological disability in young adults. In experimental animals, an experimental autoimmune/allergic encephalomyelitis (EAE) can be induced in which MS is studied. Exacerbations in EAE and MS both are dramatically mediated by cytokines and chemokines. During an exacerbation, the TNF-α family and other pro-inflammatory cytokines is highly elevated in CSF. As with all complex traits, the disorder results from an interplay between as yet unidentified environmental factors and susceptibility genes. Together, these factors trigger a cascade of events, involving engagement of the immune system, acute inflammatory injury of axons and glia, recovery of function and structural repair, post-inflammatory gliosis, and neurodegeneration. The sequential involvement of these processes underlies the clinical course characterized by episodes with recovery, episodes leaving persistent deficits, and secondary progression. Despite limited success in each of these categories, everyone touched by multiple sclerosis looks for a better dividend from applying an improved understanding of the pathogenesis to clinical management.

Now, multiple sclerosis is recognized throughout the world, with around 2 to 5 million affected individuals. For the pathologist, multiple sclerosis is a disorder of the central nervous system (CNS), manifesting as acute focal inflammatory demyelination and axonal loss with limited remyelination, culminating in the chronic multifocal sclerotic plaques from which the disease gets its name. Demyelination in MS develops by a T-cell driven inflammatory process. Thus, the primary nature of inflammation is undisputed and will remain central for treatments that modulate the immune system. There are, however, several aspects that limit the therapeutic efficacy of strategies directed exclusively against the inflammatory component of the disease. Currently, immune suppression is unable to stop the inflammatory regimes using interferon β or co-polymer I, these treatments may decrease, but do not abolish, inflammation. Furthermore, it is currently not possible to intervene more specifically in the inflammatory process because neither the trigger of inflammation (virus-induced versus autoimmunity) nor the specific target antigen in the CNS of affected patients is known.

For the patient, multiple sclerosis entails an apparently infinite variety of symptoms but with certain recurring themes and an unpredictable course. For the neurologist, multiple sclerosis is a disorder of young adults diagnosed on the basis of clinical and paraclinical evidence for a least two demyelinating lesions, affecting different sites within the brain of spinal cord, separated in time. For the clinical scientist, multiple sclerosis is the prototype inflammatory autoimmune disease of the central nervous system in which knowledge gained across a range of basic and clinical neuroscience disciplines has already allowed rational strategies for treatment. For all these groups, multiple sclerosis remains a difficult disease for which solutions seem attainable yet remain elusive.

The oligodendrocyte, a principal target of immune attack in multiple sclerosis, synthesizes and maintains the myelin sheath of up to 40 neighboring nerve axons in the central nervous system. Compact myelin consists of a condensed membrane, spiraled around axons to form the insulating segmented sheath needed for a saltatory axonal conduction: voltage-gated sodium channels cluster at the unmyelinated nodes of Ranvier, between myelin segments, from where the action potential is propagated and spreads passively down the myelinated nerve segment to trigger another action potential at the next node. The consequences of demyelination for saltatory conduction explain many clinical and laboratory features of multiple sclerosis. Partially demyelinated axons conduct impulses at reduced velocity—explaining the characteristic delays in conduction of evoked potentials. Demyelinated axons can discharge spontaneously and show increased mechanical sensitivity—accounting for the flashes of light on eye movement (phosphenes) and electrical sensation running down the spine or limbs on neck flexion (Lhermitte's symptom and sign). Partially demyelinated axons, whose safety factor for conduction is compromised, cannot sustain the fall in membrane capacitance induced by a rise in temperature, and conduction fails—leading to the characteristic appearance of symptoms and signs after exercise or a hot bath (Uhthoff's phenomenon). Ephaptic transmission (cross-talk) can arise between neighboring demyelinated axons, resulting in paroxysmal symptoms—trigeminal neuralgia, ataxia, and dysarthria, or painful tetanic posturing of the limbs, lasting one or two minutes and often triggered by touch or movement. Individuals with multiple sclerosis characteristically tire during physical and cognitive tasks, and take longer to recover: although poorly understood, and probably multifactorial, fatigue in multiple sclerosis can be very disabling, even in isolation.

Multiple sclerosis affects twice as many women as it does men; this unexplained bias is similar to that seen in many other putative autoimmune diseases. The disease has an incidence of about seven per 100,000 every year, prevalence of around 120 per 100,000, and lifetime risk of one in 400. 80% of patients present with relapsing/remitting disease and, typically, the illness passes through phases of relapse with full recovery, relapse with persistent deficit, and secondary progression. In about a quarter of patients, multiple sclerosis never affects activities of daily living; conversely, up to 15% become severely disabled within a short time. Episodes happen at random intervals, but initially average about one per year, decreasing steadily thereafter. In 20% of patients, the disease is progressive from onset, hence termed primary progressive—affecting the spinal cord and, less frequently, the optic nerve, cerebrum, or cerebellum. Disease onset is usually in the third or fourth decade, but 2% of patients with multiple sclerosis present before age 10 years, and 5% before age 16 years. In children, the distinction from acute disseminated encephalomyelitis (ADEM) can often only be established by observing the subsequent natural history. Overall, life expectancy is at least 25 years from disease onset with most patients dying from unrelated causes.

Healthy individuals harbor autoreactive myelin T-cells, presumed to normally be kept in check by regulatory T-cells. One hypothesis to explain the breakdown of immune regulation in these autoimmune diseases is molecular mimicry, which suggests that peptide (the environmental factor), presented in the groove of specific HLA/MHC class II molecules (one component of inherited risk), is immunologically indistinguishable from self-antigen and, hence, an appropriate response to infection generates inappropriate inflammation against some component of the oligodendrocyte-myelin unit. In common with all organ-specific autoimmune diseases, this systemic defect results not in a sustained autoimmune attack on the entire target organ, but, rather, in inflammatory lesions that are temporally and spatially segregated.

Failure of regulation leads to proliferation, activation, and entry into the circulation of autoreactive T-cells; they express adhesion molecules and induce reciprocal changes in endothelia, allowing access across the blood-brain barrier into the central nervous system. There, activated T-cells re-encounter antigen and activate microglia (the CNS macrophage); these, in turn, express class II molecules, re-present antigen to T-cells, and set up a proinflammatory loop, which provides an infiltrate rich in activated T-cells and microglia with some neutrophils.

Toxic inflammatory mediators are released, sustaining breakdown of the blood-brain barrier and leading to injury of axons and glia. Nitric oxide might act directly on normal or hypomyelinated axons, transiently blocking conduction and reversibly increasing deficits arising from already compromised pathways. As acute inflammation resolves, pathways are released from nitric oxide-induced physiological conduction block. Symptoms also improve as surviving functional pathways are reorganized at the cellular and systems level. Together, these mechanisms account for remission early in the disease. But tissue vulnerability is easily exposed. When compounded by high axonal firing frequency, nitric oxide cause structural (and hence irreversible) changes to axons. Axonal transection in acute inflammatory plaques is shown histologically and radiologically through reduction in the neuronal spectroscopic marker, N-acetyl aspartate (NAA). These transected axons undergo Wallerian degeneration during the subsequent 18 months, but this action does not seem to extend the lesion or shape the clinical deficit.

Cytokines and growth-promoting factors released by reactive astrocytes and microglia as part of the acute inflammatory process promote endogenous remyelinaction. But, over time, astrocyte reactivity seals the lesion and gliosis causes a physical barrier to further remyelination, reducing the capacity to accommodate cumulative deficits, and marking transition to the stage of persistent deficit.

Since permanent disability can be caused by incomplete recovery from disease episodes, relapse frequency is bound to correlate with accumulation of disability during the relapsing-remitting phase of multiple sclerosis. Type-1 interferons were first used in multiple sclerosis for their anti-viral action, in view of the propensity of viral infections to trigger relapses. In fact, their mechanism of action is immunological and complex: we prefer the evidence for functional antagonism of proinflammatory cytokines and down-regulation of class II MHC antigen expression; but other modes of action—including effects on the blood brain barrier (BBB)—can equally well be argued.

Only in trials of the two interferon β-1a preparations, not interferon β-1b, was this change in relapse rate also accompanied by reduction in the accumulation of disability. But this reduction could be accounted for by a fall in the accumulation of relapse-related deficits, rather than an effect on secondary progression.

Three other agents reduce relapse frequency, and the accumulation of disability, in relapsing-remitting multiple sclerosis; each has similar efficacy to the β-interferons and acceptable adverse effects profiles. Glatiramer acetate (Copaxone, Teva), a mixture of synthetic polypeptides was noted serendipitously to suppress experimental autoimmune/allergic encephalomyelitis, perhaps by inhibiting the binding of myelin basic protein (MBP) to the T-cell receptor or by altering the phenotype of myelin-autoreactive T-cells. The drug is licensed for the treatment of relapsing-remitting multiple sclerosis in the USA and in Europe on the basis of results from a trial of 251 patients, in which the annual relapse rate was reduced by 25% in the treated group.

Azathioprine inhibits lymphocyte proliferation by inhibiting purine synthesis, and probably has similar efficacy to the β interferons, although the trial data were obtained in a less rigorous manner and reported more candidly.

Mitoxantrone inhibits DNA repair and synthesis in dividing and non-dividing cells through inhibition of DNA topoisomerase II; it is potentially much more toxic than the β interferons, but has a USA license for the treatment of aggressive relapsing disease, including patients with high relapse frequency in the progressive phase.

In view of the fact that the ability to suppress relapses and limit their consequences is partial, no informed analyst could reasonably conclude that (despite their achievements) the β-interferons are a definitive therapy in multiple sclerosis. The pharmaceutical industry has responded by sponsoring studies with combinations of established drugs (such as β interferon and cyclophosphamide) without compelling evidence for synergistic benefit to date, together with a significant investment in novel immunotherapeutic strategies. Interferon β-1b and β-1a and glatiramer acetate are widely prescribed in North America to patients with relapsing MS. However, these drugs have significant limitations, including cost (US $11,000 per year), inconvenience (parenteral administration), frequency of adverse effects (especially "flu-like" symptoms for several hours in many patients after each injection of interferon) and a relatively modest overall impact on disease course (for example, reductions in relapse rate of less than 35%). Furthermore the therapeutic effect of interferon β more than one year after onset of treatment in relapsing-remitting MS is unclear. The National Multiple Sclerosis Society has issued a proactive directive recommending the use of these medications by all patients with clinically significant, relapsing MS. Other therapies directed against MS include the treatment of the MS patient with a (monoclonal) antibody directed against a cytokine, such as TNF-α, IL-6 or IL-12, However, although few would disagree that using these cytokine-blocking agents such as anti-TNF-α therapy may be an important therapeutic addition in the treatment of patients with MS, adverse effects related to single cytokine neutralizing therapies have emerged. Also, for unknown reasons, single cytokine blocking proteins may cause the formation of anti-dsDNA antibodies, and after repeated treatment the cumulative ANA incidence can be as high as 50%. Nonetheless, anti-TNF-α antibody therapy is associated with lupus-like symptoms. Also, demyelinizing disease and aplastic anaemia have been reported in a small number of thus treated patients. A major problem of repeated administration of chimeric therapeutic antibodies is immunogenicity, and up to 60% of antibody-treated patients develop human antichimeric antibodies (HACAs) which are related to infusion reactions and reduce therapeutic efficacy.

The invention provides a method for the treatment of a, in particular human, subject believed to be suffering of multiple sclerosis, with a specific aim to reduce the frequency, and limit the lasting effects, of relapses or exacerbations, to relieve symptoms that arise from the release of additional pro-inflammatory cytokines during the relapse, to prevent disability arising from disease progression after the relapse, and promote tissue repair after the relapse. The invention provides a pharmaceutical composition for the oral treatment during relapses in case of relapsing/remitting multiple sclerosis occurring in a subject, in particular in a human, and a method for the oral treatment during the relapses of the exacerbations associated with additional pro-inflammatory cytokine release, for example, in a primate suffering from MS or EAE comprising subjecting the subject to a signaling molecule according to the invention, preferably to a mixture of such signaling molecules. Most preferred for oral treatment during relapses is a peptide, or a mixture of peptides selected from the group of peptides LQG, QVV, PALP (SEQ ID NO:34), AQG, LAG, LQGV (SEQ ID NO:1), AQGV (SEQ ID NO:2), or LAGV (SEQ ID NO:10).

Furthermore, the invention provides a method for the prevention of the development of multiple sclerosis in a subject believed to be in need thereof, in particular for the treatment of a human being after a sign of neurological failure, such as neuritis optica has been observed but MS has not developed, and use of a signaling molecule according to the invention for the production of a pharmaceutical composition for the prevention of multiple sclerosis, for treatment of relapsing/remitting multiple sclerosis occurring in a subject, in particular in a human being, and a method for the treatment of the exacerbations associated with additional pro-inflammatory cytokine release, in particular in a human being.

Administration of such a signaling molecule or mixture preferably occurs systemically, e.g., by intravenous, intramuscular, intraperitoneal or subcutaneous administration and leads to a dampening of the effect of the additionally released pro-inflammatory cytokines during the exacerbation phase. In severe cases, intrathecal administration may be considered. However, a most preferred treatment comprises mucosal administration, preferably oral.

In a preferred embodiment, the invention provides a method for modulating relapsing/remitting disease of MS in a subject believed to be in need thereof comprising providing the subject with a signaling molecule comprising a short, gene-regulatory peptide or functional analogue thereof, wherein the signaling molecule is administered orally in an amount sufficient to modulate the iatrogenic event. The signal molecule is preferably a short peptide, preferably of at most 30 amino acids long, or a functional analogue or derivative thereof. In a much preferred embodiment, the peptide is an oligopeptide of from about 3 to about 15 amino acids long, preferably 4 to 12, more preferably 4 to 9, most preferably 3 to 4 to 6 amino acids long, or a functional analogue or derivative thereof. Of course, such a signaling molecule can be longer, for example, by extending it (N- and/or C-terminally), with more amino acids or other side groups, which can, for example, be (enzymatically) cleaved off when the molecule enters the place of final destination. In particular a method is provided wherein the signaling molecule modulates translocation and/or activity of a gene transcription factor. It is particularly useful when the gene transcription factor comprises an NFκB/Rel protein or an AP-1 protein. Many of the relapsing/remitting events as mentioned above induce increased expression of inflammatory cytokines due to activation of NFκB and AP-1, and in a preferred embodiment the invention provides a method wherein translocation and/or activity of the NFκB/Rel protein or AP-1 protein is inhibited. In one embodiment, the peptide is selected from the group of peptides LQG, AQG, LQGV (SEQ ID NO:1), AQGV (SEQ ID NO:2), LQGA (SEQ ID NO:3), VLPALP (SEQ ID NO:4), ALPALP (SEQ ID NO:5), VAPALP (SEQ ID NO:6), ALPALPQ (SEQ ID NO:7), VLPAAPQ (SEQ ID NO:8), VLPALAQ (SEQ ID NO:9), LAGV (SEQ ID NO:10), VLAALP (SEQ ID NO:11), VLPALA (SEQ ID NO:12), VLPALPQ (SEQ ID NO:13), VLAALPQ (SEQ ID NO:14), VLPALPA (SEQ ID NO:15), GVLPALP (SEQ ID NO:16), LQGVLPALPQVVC (SEQ ID NO:17), LPGCPRGVNPVVS (SEQ ID NO:18), LPGC (SEQ ID NO:19), MTRV (SEQ ID NO:20), MTR, VVC. Most preferred for oral treatment is a peptide selected from the group of peptides LQG, QVV, PALP (SEQ ID NO:34), AQG, LAG, LQGV (SEQ ID NO:1), AQGV (SEQ ID NO:2), or LAGV (SEQ ID NO:10). As said, additional expression of inflammatory cytokines is often due to activation of NFκB and AP-1. Inflammatory cytokines can be expressed by endothelium (for example, by trauma), perivascular cells and adherent or transmigrating leukocytes, inducing numerous pro-inflammatory and procoagulant effects. Together these effects predispose to inflammation, thrombosis and hemorrhage. Of clinical and medical interest and value, the present invention provides the opportunity to selectively control NFκB-dependent gene expression in tissues and organs in a living subject, preferably in a primate, allowing up-regulating essentially anti-inflammatory responses such as IL-10, and down-regulating essentially pro-inflammatory responses such as mediated by TNF-α, nitric oxide (NO), IL-5, IL-6. IL-12 and IL-1β.

In comparison with single cytokine therapy, such as the use of anti-TNF-α, anti IL-5, anti-IL-6, anti-IL-12, anti-IL-23, anti-IL-12p40, anti-IL23p40 or anti-IL-1β antibodies, using an NFκB down-regulating peptide or functional analogue thereof according to the invention has the major advantage that a major network of pro-inflammatory cytokines is down-regulated.

The invention thus provides use of an NFκB-regulating peptide or derivative thereof for the production of a pharmaceutical composition for the treatment of relapsing/remitting disease seen with MS, preferably in a primate, and provides a method of treatment of relapsing/remitting disease seen with MS, notably in a primate. It is preferred that treatment comprises administering to the subject a pharmaceutical composition comprising an NFκB down-regulating peptide or functional analogue thereof. Examples of useful NFκB down-regulating peptides are VLPALPQVVC (SEQ ID NO:21), LQGVLPALPQ (SEQ ID NO:22), LQG, LQGV (SEQ ID NO:1), GVLPALPQ (SEQ ID NO:23), VLPALP (SEQ ID NO:4), VVC, MTR and circular LQGVLPALPQVVC (SEQ ID NO:17). More down-regulating peptides and functional analogues can be found using the methods as provided herein. Most prominent among NFκB down-regulating peptides are VLPALPQVVC (SEQ ID NO:21), LQGVLPALPQ (SEQ ID NO:22), LQG, LQGV (SEQ ID NO:1), and VLPALP (SEQ ID NO:4). These are also capable of reducing production of NO by a cell.

In one embodiment, the invention provides a method of treating a subject suffering from a relapsing/remitting disease seen during relapses with MS with a method and signaling molecule according to the invention concomitantly, or at least timely, with a treatment with a single cytokine blocking protein, such as an anti-TNF-α, anti IL-5, anti-IL-6, anti-IL-12, anti-IL-23, anti-IL-12p40, anti-IL23p40 or anti-IL-1β antibody or functional analogue thereof. It is herein also provided to use a signaling molecule according to the invention for the production of a pharmaceutical composition for the treatment of a subject believed to be suffering of MS and receiving treatment with an anti-TNF-α, anti IL-5, anti-IL-6, anti-IL-12, anti-IL-23, anti-IL-12p40, anti-IL23p40 or anti-IL-1β antibody. It is herein also provided to use a composition that comprises at least two oligopeptides or functional analogues thereof, each capable of down-regulation NFκB, and thereby reducing production of NO and/or TNF-α by a cell, in particular wherein at least two oligopeptides are selected from the group LQGV (SEQ ID NO:1), AQGV (SEQ ID NO:2), and VLPALP (SEQ ID NO:4), for the treatment of relapsing/remitting disease seen with MS. In response to a variety of signals received by the body in the course of the relapsing-remitting disease seen with MS, the NFκB/Rel family of transcription factors are activated and form different types of hetero- and homodimers among themselves to regulate the expression of target genes containing κB-specific binding sites. NFκB transcription factors are hetero- or homodimers of a family of related proteins characterized by the Rel homology domain. They form two subfamilies, those containing activation domains (p65-RELA, RELB, and c-REL) and those lacking activation domains (p50, p52). The prototypical NFκB is a heterodimer of p65 (RELA) and p50 (NFκB1). Among the activated NFκB dimers, p50-p65 heterodimers are known to be involved in enhancing the transcription of target genes and p50-p50 homodimers in transcriptional repression. However, p65-p65 homodimers are known for both transcriptional activation and repressive activity against target genes. KB DNA-binding sites with varied affinities to different NFB dimers have been discovered in the promoters of several eukaryotic genes and the balance between activated NFκB homo- and heterodimers ultimately determines the nature and level of gene expression within the cell. The term "NFκB-regulating peptide" as used herein refers to a peptide or a modification or derivative thereof capable of modulating the activation of members of the NFκB/Rel family of transcription factors. Activation of NFκB can lead to enhanced transcription of target genes. Also, it can lead to transcriptional repression of target genes. Modulating comprises the up-regulation or the down-regulation of transcription. In a preferred embodiment, a peptide according to the invention, or a functional derivative or analogue thereof is used for the production of a pharmaceutical composition for oral use for the treatment of relapsing/remitting disease seen with MS. NFκB-regulating peptide can be given concomitantly to other MS treatments, the peptide (or analogue) concentration preferably being from about 1 to about 1000 mg/l, but the peptide can also been given on its own, for example, in a bolus injection. Doses of 1 to 5 mg/kg bodyweight, for example, every eight hours in a bolus injection or per infusionem until the patient stabilizes, are recommended initially, however, the potential of oral treatment allows a rapid transition to oral administration thereafter. For example, in cases where large adverse response are expected or diagnosed, it is preferred to monitor cytokine profiles, such as TNF-α, IL-6 or IL-10 levels, in the plasma of the treated patient, and to stop treatment according to the invention when these levels are normal. In a preferred embodiment it is herein provided to give a patient experiencing a severe and acute exacerbation (relapse) with a bolus injection of NFκB down-regulating peptide such as AQGV (SEQ ID NO:2), LQGV (SEQ ID NO:1) or VLPALP (SEQ ID NO:4) at 2 mg/kg and continue the infusion with an NFκB-down-regulating peptide such as AQGV (SEQ ID NO:2), LQGV (SEQ ID NO:1) or VLPALP (SEQ ID NO:4) or a functional analogue thereof at a dose of 1 mg/kg bodyweight for every eight hours. The oral treatment commences, using dosages of 0.01 to 10 mg/kg bodyweight, and preferably 0.1 to 1 mg/kg bodyweight until the relapse has stabilized. Dosages may be increased or decreased, for example, depending on the outcome of monitoring the cytokine profile in the plasma or CSF of the patient. Of course, when the relapse seems of a milder nature, oral treatment is first choice to begin with. As said, exacerbations and disease progression in experimental autoimmune/allergic encephalomyelitis (EAE) and MS both are dramatically mediated by cytokines and chemokines. During an exacerbation of MS, the TNF-α family is highly elevated in CSF and plasma. IL-12 activity is often also high. The down-regulation or T-cell regulation of these cytokines and chemokines can prevent T-cell and dendritic cells from reaching the CNS and then further down-regulate the proinflammatory response which produces demyelination of the brain and spinal cord. This model of migration of cells to the CNS and then the release of proinflammatory cytokines and chemokines is seen particularly in the course of relapsing/remitting disease and can be treated by a peptide according to the invention through NFκB regulation, the development of T-regulator cells, and the intervention of expression of early or pregenes such as C-jun or C-erg. The treatment protocols as given herein can also be used for other diseases that resemble or include exacerbations of multiple sclerosis and its variants, additional pro-inflammatory cytokine release in EAE and other infectious and/or immune based meningoencephalopathies, such as seen with measles, i.e., SSPE, mumps, infections with hemorrhagic viruses, Progressive Multifocal Encephalopathy or a papillomavirus (JC virus) disease, Bacterial Endocarditis inducing immune encephalopathy, malaria with cerebral encephalopathy, angiostrongyliasis and other parasitic encephalitis, Lyme Disease, Herpes 1-8 disease including the mono like viruses such as EBV, CMV, and HHV6, rickettsial disease, i.e., Typhus, Rocky Mountain Spotted Fever, and Q fever, Chlamydia disease, i.e., Trachoma, NSU, Chlamydial Pneumonia, mycoplasma arthritis and encephalitis, HIV-1 and 2 encephalitis and dementia, Arbovirus disease, Togavirus disease and other lentivirus or Bunya virus or Flavivirus disease. Other forms of infectious and/or inflammatory meningo-encephalomyelites are acute bacterial infections, sprirochetal infections (neurolues, lyme neuroborreliosis, tuberculosis, viral infections (enteroviruses, mumps, herpes simplex type 2, togaviruses (arbovirus), HIV type 1 and 2, HTLV-1 infections), fungal infections (*Cryptococcus neoformans, Coccidiodes immitis, Blastomyces dermatitidis, Paracoccidioides brasiliensis, sporothrix schenkii, Histoplasma capsulatum, Pseudallescheria boydii* and the dermatiaceous fungi, mostly opportunistic infections such as *candida* and *aspergillus* species and *zygomycetes*), protozoan infections (cerebral malaria, toxoplasmosis, trypanosoma species, *naegleria* species and *helminths*), neurosarcoidosis, Creutzfeldt-Jacob disease, and neurological complications following vaccination.

Mucosal and Oral Administration

Experiment 1:

Material and methods: Female NOD mice were bred and maintained in a pathogen-free facility at Lucky Farm, Balkbrug, The Netherlands. All mice were given free access to food and water.

Twenty-one to 22-week-old diabetic female NOD mice (n=5) were given four weeks long free access to either water containing 4 IU per ml hCG (pregnyl; batch number 235863) or mixture of gene-regulatory peptides LQGV (SEQ ID NO:1), GVLPALPQ (SEQ ID NO:23) and VLPALP (SEQ ID NO:4) (each 1 microgram per milliliter). Control mice were given plain water only. During these four weeks of treatment mice were daily observed for their drinking behavior, urination, and the look of the fur.

Results: During four weeks of treatment, mice without treatment drank much water because on daily bases their drinking bottle had to be refilled and they had percolated fur, what is a normal sign of heavily diabetic mice. Mice with treated water with hCG or a mixture of gene-regulatory peptides drank normal amount of water after four days of starting of the experiment and thereafter during the test period their fur was normal.

Conclusion: This experiment shows that due to oral treatment with a commercial hCG preparation as well as due to oral treatment with gene-regulatory peptides mice that were already diabetic had less sever diabetic symptoms compared to the control group. Therefore, the oral treatment of hCG preparation or gene-regulatory peptides do have visual therapeutic effects and crude hCG preparation and gene-regulatory peptides are able to be taken up in the mouth or through the digestive tract.

Experiment 2:

Material and methods: Female NOD mice were bred and maintained in a pathogen-free facility at Lucky Farm, Balkbrug, The Netherlands. All mice were given free access to food and water.

Twelve- to 14-week-old non-diabetic female NOD mice (n=14 to 16) were given seven weeks long free access to either water containing 4 IU per ml hCG from four different batches (pregnyl; batch number 235863, 248455, 293703 and 313692) or plain water only. At the end of the treatment mice were assessed for diabetes by determining the presence of glucose in urine. Mice were considered diabetic after two consecutive glucose measurements in urine.

Results: Five of the sixteen mice treated with plain water were diabetic at the end of the experiment, while two of the sixteen mice treated with batch 235863, three of the sixteen mice treated with batch 248455, one of the fourteen mice treated with batch 293703 and two of the fourteen mice treated with 313692 were diabetic.

Conclusion: This experiment shows that the oral treatment of NOD mice with a commercial hCG preparation reduce the incidence of diabetes during the treatment period. In addition, this experiment also shows the therapeutic effect of Pregnyl varies among different batches.

Experiment 3:

Material and methods: Female NOD mice were bred and maintained in a pathogen-free facility at Lucky Farm, Balkbrug, The Netherlands. All mice were given free access to food and water.

Eleven- to 13-week-old non-diabetic female NOD mice (n=9) were given five weeks long three times a week one drop (50 microliters) of water containing gene-regulatory peptides LQGV (SEQ ID NO:1), GVLPALPQ (SEQ ID NO:23) and VLPALP (SEQ ID NO:4) (each 1 microgram per milliliter) or drops of plain water. Drops were instilled in the mouth in the buccal sac. After the treatment mice were left alive for another fifteen weeks. At the age 31 to 33 weeks, mice were assessed for diabetes by determining the presence of glucose in urine. Mice were considered diabetic after two consecutive glucose measurements in urine. The mice were then sacrificed and the percentage of MP12/20 high positive bone marrow cells was determined by FACS analyses.

Result: Eight of the nine mice treated with plain water drop were diabetic at the age of 31 to 33 weeks, while five of the nine mice treated with water containing gene-regulatory peptides were diabetic at the age of 31 to 33 weeks.

Conclusion: This experiment shows that the mucosal treatment of NOD mice with gene-regulatory peptides reduces the incidence of diabetes.

Example 4

Material and Methods: Female NOD mice were bred and maintained in a pathogen-free facility at Lucky Farm, Balkbrug, the Netherlands. All mice were given free access to food and water.

Thirteen- to 14-week-old non-diabetic female NOD mice (n=10) were given five weeks long daily one drop (50 microliters) of PBS containing gene-regulatory peptides LQG, LQGV (SEQ ID NO:1), VLPALP (SEQ ID NO:4), VVC and MTRV (SEQ ID NO:20) each 20 mcg or one drop PBS only. Drops were instilled in the mouth in the buccal sac. After the oral treatment, mice were left alive for another 20 weeks. Every week mice were assessed for diabetes by determining the presence of glucose in urine. Mice were considered diabetic after two consecutive glucose measurements in urine.

Results: Nine weeks after end of the treatment, all ten mice treated orally with PBS were diabetic, while only four of the ten mice treated orally with a mixture of gene-regulatory peptides (LQG, LQGV (SEQ ID NO:1), VLPALP (SEQ ID NO:4), VVC and MTRV (SEQ ID NO:20)) were diabetic. However, anti-diabetic effect of gene-regulatory peptides seemed to be weakened over a period of time since twenty weeks after end of the treatment eight of the ten mice became diabetic.

Conclusion: This experiment shows that the oral treatment of NOD mice with a mixture of gene-regulatory peptides delayed the incidence of diabetes.

| | Diabetes incidence | |
|---|---|---|
| Age (weeks) | Group A (mixture of peptides) | Group B (PBS treatment only) |
| 13 to 14 | 0% | 0% |
| 14 to 15 | 20% | 0% |
| 15 to 16 | 20% | 10% |
| 16 to 17 | 40% | 20% |
| 17 to 18 | 40% | 30% |
| 18 to 19 | 40% | 40% |
| 19 to 20 | 40% | 100% |
| 20 to 21 | 40% | 100% |
| 21 to 22 | 40% | 100% |
| 22 to 23 | 40% | 100% |
| 23 to 24 | 40% | 100% |
| 24 to 25 | 40% | 100% |
| 25 to 26 | 40% | 100% |
| 26 to 27 | 40% | 100% |
| 27 to 28 | 80% | 100% |
| 28 to 29 | 80% | 100% |
| 29 to 30 | 80% | 100% |
| 30 to 31 | 80% | 100% |
| 31 to 32 | 80% | 100% |
| 32 to 33 | 80% | 100% |
| 33 to 34 | 80% | 100% |
| 34 to 35 | 80% | 100% |
| 35 to 36 | 80% | 100% |
| 36 to 37 | 80% | 100% |
| 37 to 38 | 80% | 100% |

Common to both type 1 and type 2 diabetes is the development of inflammatory and vascular complications that result from high glucose levels and, over time, portend significant morbidity and early mortality in affected subjects. Although multiple studies have suggested a direct role for adverse effects of glucose itself in modulating cellular properties, both in the extra- and intracellular milieu, recent observations also suggest an emerging role for the products of nonenzymatic glycoxidation of proteins and/or lipids—the advanced glycation end products (AGEs)—in the pathogenesis of diabetic complications.

A number of epidemiological studies have suggested that elevated levels of circulating insulin contribute independently to cardiovascular risk. Other factors, such as hyperlipidemia and intermittently elevated levels of blood glucose, are tightly linked to syndromes characterized by elevated levels of insulin such as metabolic syndrome or syndrome x. Activation of NFκB in the pathogenesis of atherosclerosis, ischemia-reperfusion injury, and diabetes play in this respect a special role. For example, target genes of NFκB, such as tumor necrosis factor-α (TNF-α) and vascular cell adhesion molecule-1, have long been speculated to participate in the earliest stages of atherogenesis. Indeed, RelA/p65, one of the components of NFκB, has been identified within the nuclei of vascular smooth muscle cells (VSMCs) and mononuclear phagocytes in human atheromata.

One of the consequences of hyperglycemia in both type 1 and type 2 is the generation of advanced glycation end products (AGEs). Interaction of these products of nonenzymatic glycation/oxidation of proteins, with their key signal transduction receptor RAGE (receptor for AGE), results in activation of NFκB in endothelial cells, mononuclear phagocytes, and VSMCs, by processes that involve, at least in part, generation of reactive oxygen intermediates and activation of $p21^{ras}$ and ERK1/2 kinases. Recently, a specific AGE, carboxy(methyl lysine) adducts of proteins, has been shown to bind RAGE and mediate cellular activation, both in vitro and in vivo. Evidence definitively linking RAGE to these ligand-mediated effects was demonstrated by blockade of AGE-mediated activation of NFκB in the presence of blocking antibodies to RAGE, soluble RAGE (sRAGE; the extracellular ligand-binding domain), or transient transfection into wild-type RAGE-bearing cells of a construct in which solely the cytosolic domain of the receptor was deleted. In the latter case, a dominant-negative effect resulted, as AGE-stimulated activation of NFκB was significantly suppressed. Furthermore, a novel property of insulin is its ability to activate prenyl transferases, farnesyl transferases, and geranylgeranyl transferases I and II. Because these molecules possess the capacity to post-translationally modify Ras, Rho, and Rab proteins, their activation links them to signal transduction pathways. Incubation of VSMCs with insulin (largely at physiologically relevant doses) increased availability of geranylgeranylated Rho-A, thereby invoking an established mechanism to link increased levels of insulin to activation of NFκB. In VSMCs, insulin, and AGEs, hyperglycemia or angiotensin II synergized to enhance NFκB activation to even greater degrees than that observed by any of these mediators alone. It is also known that insulin primes the vasculature for enhanced activation on contact with these traditional mediators; the vascular microenvironment in type 2 diabetes or syndromes of insulin resistance is enriched in factors that appear to lead to a common pathway, activation of NFκB. In above experiments the oral treatment of pre-diabetic NOD mice with gene-regulatory peptides reduced the incidence of diabetes showing an inhibitory effect of the treatment on pancreatic inflammation, β-cell destruction and on autoimmune process. Furthermore, when the treatment was started at late stage in diabetes (in already diabetic mice), we observed the inhibition of inflammatory effects of prolonged hyperglycemia and reduction of clinical symptoms of inflammation which was observed by their changes in drinking behavior, reduction in urination, and the look of the fur. The ongoing impairment of glucose tolerance and/or prolonged hyperglycemia which with time if uncontrolled in patients results in serious diabetic complications such as kidney failure/damage, impaired blood macro- and microcirculation, retinopathy, neuropathy, nephropathy and accelerated arteriosclerosis was thus countered by mucosal treatment with gene-regulatory peptides directed at down-regulation of NFκB. NFκB is a target to prevent or suppress the vascular-perturbing properties of a range of injurious molecules linked to diabetes and insulin resistance, from oxidized lipoproteins, to AGEs, to high levels of glucose or insulin. NFκB is a pleiotropic transcription factor. In the context of both type 1 and 2 diabetes (hyperinsulinemia and hyperglycemia), a range of environmental stimuli, such as AGEs, hyperglycemia, and angiotensin II triggers signal transduction pathways leading to NFκB activation. Prominently included among these signaling mechanisms is a role for Ras, Rho-A, cdc42, and Rac1. Nuclear translocation of NFκB leads to activation of a range of genes involved in host and cellular defense responses. In certain settings, activation of NFκB may lead to "good" inflammation, manifested by resolution and regeneration, or "bad" inflammation, causing tissue destruction. However, it is likely that separation of good from bad inflammation triggered by NFκB will be difficult because mechanisms underlying both operate in tandem, delicately balanced, under many conditions. Our gene-regulatory peptides have regulatory effects on, for example, NFκB in this respect and play an important therapeutic role.

FURTHER REFERENCES

WO99/59617; WO01/72831; WO97/49721; WO01/10907; WO01/11048 EP 1 138 692; US 2002/0064501; Khan et al., *Human Immunology* 63:1-7, 2002; Christman et al., *Intens. Care Med.* 24:1131-1138, 1998; Tak et al., *J. Clin. Invest.* 107:7-11, 2001; EP 1 300 418; U.S. Pat. Nos. 5,851, 997; 6,319,504 B1; Blackwell et al., *Am. J. Respir. Cell Mol. Biol.* 17:3-9, 1997; WO01/10907; U.S. Pat. Nos. 6,319,504; 6,489,296; WO02/085117; WO98/35691; DE 3715662; Patil et al., *Acta Neurochirurgica* 87:76-78,1987; Slater et al., *Transplantation* 23:104-104, 1977; Blackwell et al., *Am. J. Respir. Cell Mol. Biol.* 17:3-9, 1997; WO99/59617; Tan et al., *Acta Physiol. Sinica.* 55:58-64, 2003; US 2002/0041871; DE 19953339; Jyonouchi Harumi et al., *J. Neuroim.* 120:170-179, 2001; Khan et al., *Human Immunology* 62:1315-1323, 2001; Roehrig et al., *Zentralblatt Bakt* 289:89-99, 1999; Tovey et al., *J. Interferon Cytokine Res.* 19:911-921, 1999; Kanungo et al., *J. Adv. Zool.* 20:1-5, 1999; Khan et al., *Human Immunology* 63:1-7, 2002; Muchmore and Blaese, *J. Immunol.* 118: 881-886, 1977; Muchmore et al., *J. Exp. Med.* 160:1672-1685, 1984; U.S. Pat. No. 4,977,244.

What is claimed is:

1. A method of treating type I diabetes in a subject, the method comprising administering to the subject an effective amount of a pharmaceutical composition consisting of a pharmaceutically acceptable diluent and a peptide selected from the group consisting of SEQ ID NO: 1, SEQ ID NO: 4, SEQ ID NO: 23, and combinations thereof.

2. The method according to claim 1, wherein the pharmaceutical composition is in a form for mucosal application and wherein said treatment of a subject comprises a systemic treatment.

3. The method of claim 1, wherein the pharmaceutical composition is in a form for oral administration.

* * * * *

SEQUENCE LISTING

```
<160> NUMBER OF SEQ ID NOS: 34

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Gln Gly Val
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Gln Gly Val
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 3

Leu Gln Gly Ala
  1

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Leu Pro Ala Leu Pro
  1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Leu Pro Ala Leu Pro
  1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Ala Pro Ala Leu Pro
  1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Leu Pro Ala Leu Pro Gln
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Leu Pro Ala Ala Pro Gln
  1               5
```

```
<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Leu Pro Ala Leu Ala Gln
 1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Ala Gly Val
 1

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Leu Ala Ala Leu Pro
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Leu Pro Ala Leu Ala
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Leu Pro Ala Leu Pro Gln
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 14

Val Leu Ala Ala Leu Pro Gln
  1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Leu Pro Ala Leu Pro Ala
  1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Val Leu Pro Ala Leu Pro
  1               5

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Gln Gly Val Leu Pro Ala Leu Pro Gln Val Val Cys
  1               5                  10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Pro Gly Cys Pro Arg Gly Val Asn Pro Val Val Ser
  1               5                  10

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Pro Gly Cys
  1
```

```
<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Thr Arg Val
  1

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Leu Pro Ala Leu Pro Gln Val Val Cys
  1               5                  10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Gln Gly Val Leu Pro Ala Leu Pro Gln
  1               5                  10

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Val Leu Pro Ala Leu Pro Gln
  1               5

<210> SEQ ID NO 24
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Val Val Cys Asn Tyr Arg Asp Val Arg Phe Glu Ser Ile Arg Leu Pro
  1               5                  10                  15

Gly Cys Pro Arg Gly Val Asn Pro Val Val Ser Tyr Ala Val Ala Leu
             20                  25                  30

Ser Cys Gln Cys Ala Leu
         35
```

-continued

```
<210> SEQ ID NO 25
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Pro Arg Cys Arg Pro Ile Asn Ala Thr Leu Ala Val Glu Lys Glu
 1               5                  10                  15

Gly Cys Pro Val Cys Ile Thr Val Asn Thr Thr Ile Cys Ala Gly Tyr
             20                  25                  30

Cys Pro Thr
        35

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Lys Ala Pro Pro Pro Ser Leu Pro Ser Pro Ser Arg Leu Pro Gly
 1               5                  10                  15

Pro Ser

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Ile Arg Leu Pro Gly Cys Pro Arg Gly Val Asn Pro Val Val Ser
 1               5                  10                  15

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
agctcagagg gggactttcc gagag                                              25

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Val Val Cys
 1
```

```
<210> SEQ ID NO 30
<211> LENGTH: 17
<212> TYPE: PRT
<213> ORGANISM: artificial
<220> FEATURE:
<223> OTHER INFORMATION: Synthetic peptide

<400> SEQUENCE: 30

Met Thr Arg Val Leu Gln Gly Val Leu Pro Ala Leu Pro Gln Val Val
1               5                   10                  15

Cys

<210> SEQ ID NO 31
<211> LENGTH: 21
<212> TYPE: PRT
<213> ORGANISM: Artificial
<220> FEATURE:
<223> OTHER INFORMATION: Synthetic peptide

<400> SEQUENCE: 31

Cys Ala Leu Cys Arg Arg Ser Thr Thr Asp Cys Gly Gly Pro Lys Asp
1               5                   10                  15

His Pro Leu Thr Cys
            20

<210> SEQ ID NO 32
<211> LENGTH: 18
<212> TYPE: PRT
<213> ORGANISM: Artificial
<220> FEATURE:
<223> OTHER INFORMATION: Synthetic peptide

<400> SEQUENCE: 32

Cys Arg Arg Ser Thr Thr Asp Cys Gly Gly Pro Lys Asp His Pro Leu
1               5                   10                  15

Thr Cys

<210> SEQ ID NO 33
<211> LENGTH: 37
<212> TYPE: PRT
<213> ORGANISM: Artificial
<220> FEATURE:
<223> OTHER INFORMATION: Synthetic peptide

<400> SEQUENCE: 33

Thr Cys Asp Asp Pro Arg Phe Gln Asp Ser Ser Ser Ser Lys Ala Pro
1               5                   10                  15

Pro Pro Ser Leu Pro Ser Pro Ser Arg Leu Pro Gly Pro Ser Asp Thr
            20                  25                  30

Pro Ile Leu Pro Gln
        35

<210> SEQ ID NO 34
<211> LENGTH: 4
<212> TYPE: PRT
<213> ORGANISM: Artificial
<220> FEATURE:
<223> OTHER INFORMATION: Synthetic peptide

<400> SEQUENCE: 34

Pro Ala Leu Pro
1
```